United States Patent
Hasselmann et al.

(10) Patent No.: US 11,578,305 B2
(45) Date of Patent: Feb. 14, 2023

(54) STRUCTURED COMPOSITE OF MATRIX MATERIAL AND NANOPARTICLES

(71) Applicant: Fraunhofer-Gesellschaft zur Förderung der angewandten Forschung e.V., Munich (DE)

(72) Inventors: Sebastian Hasselmann, Wuerzburg (DE); Doris Heinrich, Mespelbrunn (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 685 days.

(21) Appl. No.: 16/479,800

(22) PCT Filed: Jan. 29, 2018

(86) PCT No.: PCT/EP2018/052026
§ 371 (c)(1),
(2) Date: Jul. 22, 2019

(87) PCT Pub. No.: WO2018/141657
PCT Pub. Date: Aug. 9, 2018

(65) Prior Publication Data
US 2021/0340492 A1 Nov. 4, 2021

(30) Foreign Application Priority Data
Jan. 31, 2017 (DE) .......................... 102017101823.9

(51) Int. Cl.
*C12N 5/00* (2006.01)
*B33Y 70/00* (2020.01)
(Continued)

(52) U.S. Cl.
CPC ............ *C12N 5/0068* (2013.01); *B33Y 70/00* (2014.12); *B82Y 5/00* (2013.01); *B82Y 30/00* (2013.01);
(Continued)

(58) Field of Classification Search
None
See application file for complete search history.

(56) References Cited

U.S. PATENT DOCUMENTS

| 7,655,376 B2 | 2/2010 | Anderson et al. |
| 10,259,829 B2 | 4/2019 | Wolter et al. |

(Continued)

FOREIGN PATENT DOCUMENTS

| EP | 1196478 B1 | 8/2003 |
| WO | 2006/099333 A2 | 9/2006 |

(Continued)

OTHER PUBLICATIONS

Jia et al., Adv. Mater. 22: 2463-2467 (2010).*
(Continued)

*Primary Examiner* — Erin M. Bowers
(74) *Attorney, Agent, or Firm* — Duane Morris LLP

(57) ABSTRACT

The present invention provides a composite which can be produced by photostructuring a photostructurable matrix material in a composite formulation to form a structured matrix with nanoparticles, where the refractive index of the composite with nanoparticles differs from the refractive index of the composite without nanoparticles at one wavelength, selected from the range from 150 nm to 2000 nm by less than 0.5, said composite being hierarchically structured and comprising at least one structural unit (I) of a selected thickness (i) and structural units (II) branching from said structural unit (I) of a selected thickness (ii), wherein the thickness (ii) at the branch-off points is at most half the
(Continued)

thickness (i). In addition, the present invention provides an improved process for the preparation of a composite comprising photostructured matrix material and nanoparticles contained therein and the use of the composite.

15 Claims, 13 Drawing Sheets

(51) Int. Cl.
 B82Y 5/00 (2011.01)
 B82Y 30/00 (2011.01)
 B82Y 40/00 (2011.01)
(52) U.S. Cl.
 CPC ........... B82Y 40/00 (2013.01); C12N 2533/10 (2013.01); C12N 2533/30 (2013.01)

(56) References Cited

U.S. PATENT DOCUMENTS

| | | |
|---|---|---|
| 2003/0013047 A1 | 1/2003 | Tani |
| 2009/0258197 A1 | 10/2009 | Hino et al. |
| 2010/0120145 A1 | 5/2010 | Brunner et al. |
| 2014/0080061 A1 | 3/2014 | Redinger et al. |

FOREIGN PATENT DOCUMENTS

| | | |
|---|---|---|
| WO | 2012/041519 A2 | 4/2012 |
| WO | 2014/108538 A2 | 7/2014 |

OTHER PUBLICATIONS

Ruth Houbertz et al. (2003), "Inorganic-organic hybrid materials for application in optical devices," Thin Solid Films 442, 194-200.
Buestrich R. et al. (2001), ORMOCER® s for Optical Interconnection Technology, Journal of Sol-Gel Science and Technology 20, 181-186.
Gorelashvili et al., Amoeboid migration mode adaption in quasi-3D spatial density gradients of varying lattice geometry, New Journal of Physics, 16, 2014.
Baohua Jia et al., "Highly Non-Linear Quantum Dot Doped Nanocomposites for Functional Three-Dimensional Structures Generated by Two-Photon Polymerization," Advanced Materials, vol. 22, No. 22, Jun. 11, 2010.
R. Houbertz et al., "Investigations on the generation of photonic crystals using two photon polymerization (2PP) of inorganic-organic hybrid polymers with ultra-short laser pulses," Physica Status Solidi. A: Applications and Materials Science, vol. 204, No. 11, Nov. 1, 2007, pp. 3662-3675.
Baohua Jia et al., "Functional three-dimensional nonlinear nanostructures in a gold ion nanocomposite," Quantum Electronics Conference &Lasers and Electro-Optics (CLEO/IQEC/PACI FIC RIM), 2011, IEEE, Aug. 28, 2011, pp. 214-215.
Andrey L Stepanov et al., "Synthesis and optical properties of silver nanoparticles in Ormocer", Applied Physics A; Materials Science & Processing, Springer, Berlin, DE, vol. 108, No. 2, Mar. 28, 2012, pp. 375-378.
Ruth Houbertz et al., "Advanced packaging materials for optical applications: bridging the gap between nm-size structures and large-area panel processing," Proceedings Optical Diagnostics of Living Cells II, vol. 6126, Feb. 9, 2006.

* cited by examiner (A) (B)

(A)            (B)

(A)

(B)

(A)

(B)

(A)

(B)

STRUCTURED COMPOSITE OF MATRIX MATERIAL AND NANOPARTICLES

FIELD OF INVENTION

The present invention concerns a composite of structured matrix material and nanoparticles, a process for producing the composite and the use of the composite.

STATE OF THE ART

In the field of cell culture, tissue engineering and lab-on-a-chip systems, scaffolds are needed to imitate the natural environment of biological cells and to control cell behavior such as proliferation, adhesion or differentiation. By varying the surface roughness, the structuring in the micrometer range or the chemical surface functionalization, it is possible, for example, to influence the behavior of biological cells. So far it has not been possible to produce scaffolds with sizes in the centimeter range with a resolution down to the nanometer scale within a sample. In particular, this is not possible in combination with any three-dimensional structurability. In addition, it is a great advantage for biomaterials to increase the contact surface and surface roughness without changing the macroscale three-dimensional structure.

There are numerous state-of-the-art materials that can be used as biological scaffold structures, e.g. hydrogels, glass or fibers. In some cases it is also possible to produce these using 3D printing, lithography or MPP processes. The polymerization process using multi-photon polymerization (MPP) or two-photon polymerization (2PP) is now used in many areas.

Mesoporous nanoparticles can be used as drug delivery systems. $TiO_2$ particles are used to adjust the surface roughness, but without matrix or 3D structuring.

DE 10 2007 020 302 B4 describes 3D cell cultures in which various nanoparticles are embedded. These can be functionalized or released with a delay. Structures are to be produced using a contactless printing process, an electrospinning or LIFT process.

WO 2012/041519 A2 reveals a material that is biocompatible and biofunctionalized, from which 2D and 3D structures can be produced for medical technology. It is also photostructurable (SL, 3D printing or MPP). Biofunctional groups (growth factors, antibodies, peptides, etc.) can be incorporated into the polymer. In one embodiment, the biofunctional components are covalently or non-covalently bound to the matrix via nanoparticles. The nanoparticles can have cavities that are filled with active ingredients and can be released.

US 2014/0080061 A1 reveals a composite material that can be cross-linked with TPA and contains functionalized nanoparticles (including silica). Through functionalization, the particles can be covalently bound to the matrix.

Problems to be Solved by the Invention

Therefore, it is not possible to produce scaffolds with sizes in the centimeter range with a resolution down to the nanometer scale within a sample using state-of-the-art technology.

In particular, this is not possible in combination with any three-dimensional structurability and an increase in the contact surface and surface roughness without simultaneously changing the macroscale three-dimensional structure.

More specifically, the state of the art does not reveal the combination of hierarchical structure of the structures with high accuracy and simultaneous incorporation of nanoparticles into the structures, as well as the simultaneous adjustment of surface roughness, especially to a high value, by addition of nanoparticles.

Therefore, the problem underlying this invention is to provide an improved and simple process for the production of composites containing structured material and nanoparticles.

SUMMARY OF THE INVENTION

The problem was solved by providing a composite comprising photostructured matrix material and nanoparticles contained therein, whereby the refractive index of the structured material and the refractive index of the nanoparticles are matched. Another aspect of the invention is an improved process for the production of a composite and the use of the composite for medical or biological purposes.

The subject-matter of the present invention is, in particular, the following:

[1] A composite, obtainable by photostructuring a photostructurable matrix material in a composite batch containing said photostructurable matrix material and nanoparticles to form a structured matrix having nanoparticles contained therein, wherein the refractive index of said composite having nanoparticles differs by less than 0.5 from the refractive index of said composite having no nanoparticles at a wavelength selected from the range of 150 nm to 2000 nm, wherein the composite is hierarchically structured and comprises at least one structural unit (I) of a thickness (i) selected from the range of 10 µm to 100 mm and structural units (II) branching off from the structural unit (I) of a thickness (ii) respectively selected from the range of 100 nm to 1000 µm, wherein the thickness (ii) at the branch-off points is at most half the thickness (i).

[2] The composite according to point [1], which comprises at least one structural unit (I) of a thickness (i) selected from the range of 100 µm to 50 mm, structural units (II) branching off from the structural unit (I) of a thickness (ii) respectively selected from the range of 10 µm to 1000 µm, and structural units (III) branching off from the structural units (II) of a thickness (iii) respectively selected from the range of 100 nm to 100 µm, wherein the thickness (ii) of the structural units (II) at the branch-off points from the structural unit (I) is at most half the thickness (i) the thickness (iii) of the structural units (III) and at the branch-off points from the structural units (II) is at most half the thickness (ii).

[3] The composite according to point [1] or [2], wherein a plurality of structural units (I), (II) and (III) and a plurality of branches of the structural units (II) branching off from (I) and (III) branching off from (II) are present.

[4] The composite according to any of the preceding points, wherein structural units (I), (II) and (III) are each independently planar.

[5] The composite conforming to one of the preceding points, the inner surface of which is at least twice as large as the outer surface.

[6] The composite according to one of the preceding points whose surface roughness $Z_q$ determined by scanning force microscopy is 1 to 100 nm.

[7] The composite according to one of the preceding points, wherein the mean size $D_{n,50}$ of the nanoparticles is selected from the range of 10 to 1000 nm.

[8] The composite according to any of the preceding points, wherein the matrix formed by the photostructured matrix material has a structure whose size is selected from the range of 0.1 to 100 µm, wherein the structural size of the matrix and the size of the nanoparticles are selected such that a plurality of nanoparticles may each be contained in the voids of the matrix.

[9] The composite according to one of the preceding points, wherein the nanoparticles are contained in a volume fraction of 10 to 60% and the average size of the nanoparticles is selected from the range of 30 to 600 nm.

[10] A process for preparing a composite according to any one of points [1] to [9] containing structured matrix material and nanoparticles contained therein comprising the steps of:
(a) a step in which a composite composition comprising a photostructurable material and nanoparticles is provided,
(b) a step in which at least one polymerization reaction is carried out by irradiating the photostructurable material to form a matrix to obtain the composite,
characterized in that the refractive index of the nanoparticle composite composition differs from the refractive index of the nanoparticle-free composite composition by less than 0.5 at the wavelength of irradiation performed in the at least one polymerization reaction in step (b).

[11] The process according to point [10], wherein step (b) comprises two polymerization reactions when structural units (I) and (II) are formed or three polymerization reactions when structural units (I), (II) and (III) are formed, wherein in each of the respective polymerization reactions a part of the photopolymerizable materials is reacted.

[12] The method according to point [11], wherein the two or three polymerization reactions are effected by the presence of different photostructurable materials and/or by variation of at least one process parameter selected from irradiation wavelength, irradiation power density and irradiation duration.

[13] The process according to any one of points [10] to [12], wherein structural units (I) are formed by a polymerization reaction and structural units (II) are formed by a further polymerization reaction and, if present, structural units (III) are formed by a further polymerization reaction.

[14] A composite obtainable by a process according to any of points [10] to [14].

[15] Use of the composite according to any of points [1] to [9] or [14] as a scaffold for biological cells.

Advantages of the Invention

The advantages of the method according to the invention are the provision of a hierarchical structure with high accuracy and simultaneous incorporation of nanoparticles. In particular, a higher concentration of nanoparticles can be used by the inventive process while maintaining the accuracy of the structure.

With regard to the hierarchical structure, the method according to the invention allows various photostructuring processes to be combined within a sample and thus structures being in a centimeter scale (e.g. 3D printing) to be provided with a (sub)micrometer structure (MPP or 2PP). The structure additionally shows an intrinsic nanostructuring of the surface by nanoparticles. By selecting the 3D scaffold geometries and particle sizes, any 3D scaffolds or structures can be created. By selecting the nanoparticles and the photostructurable material, a composition can be provided for the photostructuring process in which the refractive indices of the components are adjusted, in particular to a value so similar that the desired accuracy of the photostructuring is made possible.

Being a hierarchical structure, the structure of the composite makes it possible to provide systems that are very stable on the one hand and have a high inner surface on the other. In addition, the combination of different structuring methods makes it possible to produce samples much more efficiently in terms of time and cost.

With regard to the adjustable surface roughness, the choice of nanoparticles (size, material, porosity, etc.) can also be used to control a wide variety of intrinsic properties of 2D/3D structures, such as those that can be used to influence cell behavior. These include surface roughness, drug release, surface chemistry, antimicrobial and the like. In combination with microfluidic systems, lab-on-a-chip or organ-on-a-chip systems with customized properties can be produced for a wide variety of applications. Using a biodegradable matrix, 3D scaffolds for implants can also be produced, which can also be used as drug delivery systems using particles charged with active substances.

With regard to the high surface roughness, the nanoparticles and the photostructurable material can be selected in such a way that the refractive indices differ only slightly. Thus, a high accuracy of the photo structuring is possible. By adjusting the refractive indices, it is possible to use a high concentration of nanoparticles and still achieve a high accuracy of photostructuring.

The adjustment of the refractive indices enables a wider range of combinations of photostructured material and nanoparticle properties.

An exemplary composite according to the invention that contains silica, ORMOCER® I (see Table 3), was found to be non-cytotoxic in a test according to ISO 10993, making it suitable for use as a medical device due to its biocompatibility.

A further criterion for use in the field of medical technology, especially with implants, is sterilizability. The composite used as an example in this invention can be autoclaved without structural or topographical changes. In addition to this sterilization option, the composite systems can also be treated with a 70% ethanol/water mixture or by gamma/UV irradiation.

It was also shown that the cell behaviour can be influenced by TPA through the nanoparticle size used, the surface topography and the surface structuring in the micrometer range.

When hollow particles are used within a biodegradable matrix, cell behaviour can be specifically influenced by the use of nutrients, growth factors or other active substances. The active ingredient is gradually released during the degradation of the matrix. This concept is shown schematically in FIG. 2 and described in detail in the examples and FIG. 16.

FORMS OF EXECUTION OF THE INVENTION

Figure 1:
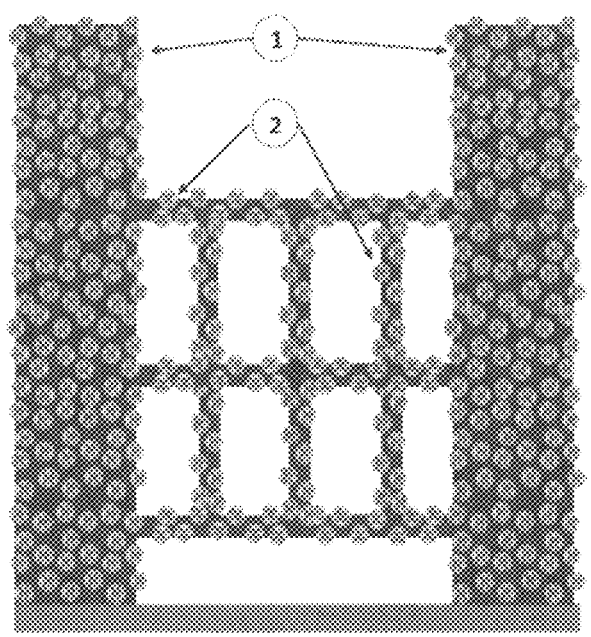
FIG. 1 shows a schematic cross-section of a possible 3D scaffold design, which was created by combining several photostructurable processes. This makes it possible to adapt a hierarchical structure from the centimeter to the nanometer range.

The term "photostructurable material" or "photostructurable matrix material" used here covers any material or composition of different materials that can be polymerised by treatment with electromagnetic radiation. The electromagnetic radiation can, for example, be formed by a focused light or by a laser beam. The material can be a precursor of a polymer, such as a monomer. An example of a photostructurable material is an ORMOCER®, i.e. a hydrolytically condensed silane compound that carries organically cross-linkable groups.

The photostructurable material may contain different photostructurable materials. On the one hand, this can mean that two or more materials of different structure, for example different polymer precursors, can be contained as a mixture. On the other hand, it may also mean that there are different photostructurable groups in the same compound, for example reactive groups of different structure and photoreactivity in a single polymer precursor molecule.

In the context of this invention, "scaffold structure" or "scaffold" preferably means a three-dimensional matrix, preferably with pores or interstices. The structure can be used for attaching cells. A scaffold structure within the scaffold of the present invention is, in particular in its preferred embodiment, a structure which not only allows cells to adhere or adhere to the surface, but also in particular allows cells to grow into or integrate into the scaffold structure itself.

In this invention, structures or three-dimensional scaffold structures of different size ranges are formed. For example, structures are produced in the millimeter, micrometer, submicrometer or nanometer range. The specification of a size value of a structure means that free spaces, pores or cavities are created in the structure which have the dimensions of the specified value at least in one spatial direction, i.e. in length, width or depth. Preferably a structure with pores is created whose dimensions correspond to this size value. If, for example, a structure in the range of 1 to 100 µm is formed, this means that pores of a size of about 1 to 100 µm are formed. The same applies to the other specifications of size values for structures used here.

The invention-based composite has a hierarchical structure and has, for example, the following three hierarchy levels:
Level 1: a superstructure of a size from 10 µm to 100 mm, preferably 100 µm to 50 mm, more preferably 500 µm to 5 mm;
Level 2: a fine structure of size 100 nm to 1000 µm, preferably 1000 nm to 100 µm, more preferably 5 µm to 50 µm;
Level 3: Nanoparticles of size 1 to 1000 nm, preferably 5 to 800 nm, more preferably 10 to 500 nm.

In any case, the respective superstructure has such large free spaces or pores that a multitude of desired fine structures can be formed in it. And in any case, the respective fine structure has such large free spaces or pores that it can contain a multitude of nanoparticles. The term "multitude" means at least 5, at least 10, at least 50 or at least 100 or 5 to 1000, preferably 10 to 500, more preferably 20 to 300 and most preferably 30 to 100, in other words multitude means that the structure in at least one spatial direction, preferably at least two spatial directions, i.e. in length, width or depth direction, has an extent which is greater than the mean size of the nanoparticles by a factor of 5 to 1000, preferably 5 to 100 or 10 to 1000, more preferably 5 to 50 or 10 to 100.

The composite according to the invention is hierarchically structured. This means that it has thicker and less thick structural units. The less thick, i.e. thinner, structural unit branches off from the thicker structural unit. This junction, i.e. the branch, can assume any angle, but is preferably 90°, so that a T-shaped structure is created. Such a structural unit is an area of a structure of any size, but is preferably the entire structure that begins at a branch and ends, if present, at the next branch, that is, the section between two branches. In a spatial system having coordinates in x, y and z directions, the thickness of a given structural unit in a three-dimensional composite system is defined as the smallest value of the values of x, y and z. In a planar structural unit having a length x and a width y, the thickness is thus the extent in z direction. If one structural unit branches off from another, a separate room system with x, y or z direction applies to each structural unit independently of the other structural unit. This means that for two structural units, the thickness direction of the first structural unit does not have to have the same direction in space as the thickness direction of the second structural unit. Of course, the hierarchical arrangement with the branches does not exclude other structural elements, for example, a branch or intersection of structural units on the same hierarchy level. The dimensions of the structural units are preferably determined without taking into account any nanoparticles present and protruding from the structural unit.

The dimensions of the respective structural areas can be adjusted by adjusting the process parameters during photo-structuring. In a given composite, the dimensions can be determined by scanning electron microscopy.

Examples of hierarchical structuring are given in US 2003/0013047 A1, where, for example, section [0012] describes a process in which first coarse processing with single-photon polymerization and then fine processing with two-photon polymerization are described.

The hierarchical structure in the composite is defined by at least two hierarchy levels. A structural unit (I) represents the superior hierarchy level, structural unit (II) follows as the next hierarchy level, and structural unit (III) represents the lowest of the three levels. The number of hierarchy levels is of course not limited to three. The additional surface produced by the nanoparticles represents a further hierarchical level.

In the embodiment (A1) having at least two hierarchical levels, the composite contains at least one structural unit (I) of a thickness (i) selected from the range from 10 µm to 100 mm and structural units (II) branching off from the structural unit (I) of a thickness (ii) each selected from the range from 100 nm to 1000 µm, the thickness (ii) at the branch-off points being at most half the thickness (i).

In the embodiment (A2) having at least three hierarchical levels, the composite comprising at least one structural unit (I) of thickness (i) selected from the range of 100 µm to 100 mm, structural units (II) of thickness (ii) selected from the range of 10 µm to 1000 µm branching from the structural unit (I), and structural units (III) of thickness (iii) selected from the range of 100 nm to 100 µm branching from the structural units (II), respectively, wherein at the branch-off points of the structural units (II) from the structural unit (I) the thickness (ii) is at most half the thickness (i) and at the branch-off points of the structural units (III) from the structural units (II) the thickness (iii) is at most half the thickness (ii).

The thickness of the structural unit of a lower hierarchical level is at most half of the thickness of the respective higher hierarchical level, i.e. (iii) in relation to (ii) and (ii) in relation to (i), and in further embodiments at most one third, at most one quarter or at most one tenth. These thickness ratios apply to the branching points, but preferably also to the remaining areas of the respective structural units.

In the embodiment (A1), the thickness range (i) is preferably 100 µm to 10 mm, more preferably 100 µm to 5 mm, and the thickness range (ii) is preferably 1000 nm to 100 µm, more preferably 1000 nm to 50 µm. Preference is given to an execution embodiment (A1) with the combination of the respective preferred areas mentioned, more preference is given to an execution embodiment (A1) with the combination of the respective preferred areas mentioned.

In embodiment (A2) the thickness range is (i) preferably 500 µm to 10 mm, more preferably 1000 µm to 5 mm, the thickness range (ii) preferably 50 to 500 µm, more preferably 100 to 500 µm, and the thickness range (iii) preferably 1000 nm to 100 µm, more preferably 1000 nm to 50 µm. Preference is given to an embodiment (A2) with the combination of the respective preferred areas, more preference is given to an embodiment (A2) with the combination of the respective more preferred areas.

The structural units (I), (II) and (III) can be produced using the same or different structuring processes. One can use any known structuring procedure for each structure hierarchy level. For the skilled person, however, limitations clearly result from the fact that certain structuring processes are better or simpler to carry out for certain thicknesses of structural units or that only certain structuring processes are suitable at all.

By combining different photostructuring methods, desired hierarchical structures can be created. In this way, a hierarchical structure from the centimeter to the nanometer range can be adapted at will. For example, superstructures in the centimeter range can be realized by rapid prototyping or 3D printing, structures in the millimeter to micrometer range by lithography and structures in the submicrometer range by MPP.

The inventive process comprises the steps (a) and (b) described above. The polymerization reactions used in step (b) to form structural units (I) and (II) or (I), (II) and (III) can be carried out simultaneously or successively. If they are carried out at the same time, the respective structural units at the interfaces connect through the simultaneous polymerization of the starting materials. If they are carried out one after the other, the respective structural units at the interfaces also combine, since polymerisation can be carried out by selecting the starting materials and process parameters in such a way that incomplete cross-linking occurs. Examples of typical degrees of crosslinking are in the range of 60 to 80%. The unreacted reactive groups can then be used in the subsequent polymerization of a further structural unit to covalently link the newly polymerized with the existing structural unit. It may be particularly advantageous to carry out the polymerisation successively if a different photostructuring process is used for the formation of a structural unit than for the formation of a further structural unit. An example is the formation of a structural unit (I) using 3D printing and the subsequent formation of a structural unit (II) using MPP.

Sequential structuring processes can also be used if a change in the starting materials and/or the process parameters is to be made. For example, a particularly stable structural unit (I) made of photostructurable material without the addition of nanoparticles is produced as a superordinate scaffold structure in one embodiment. Afterwards, the unreacted material is removed and a composite preparation containing photostructurable material and nanoparticles is added to the scaffold structure. This composition can then be polymerised by forming structural units (II) and possibly (III) and incorporating nanoparticles. In this embodiment, a structural unit of the invented composite is manufactured before stage (a). FIG. 5(B) shows that the structural unit produced without nanoparticles is at least superficially covered with nanoparticles through the use of nanoparticles in the subsequent reaction.

However, in other forms of the composite invention, both the structural units (I) and the structural units (II) and, if appropriate, (Ill) have been prepared or can be prepared from the composite batch from photostructurable matrix material and nanoparticles so that nanoparticles are present in all these structural units.

Due to its hierarchical structure, the composite according to the invention has a large inner surface. The inner surface can be determined with suitable microscopic methods by evaluating cross-sections of the composite. In addition to the large inner surface, the total surface of the composite is also increased by the large surface roughness of the composite due to the presence of nanoparticles. By appropriate selection of the measurement accuracies and the evaluation parameters, in particular the resolution, the microscopic methods can be used to determine the inner surface of the composite either taking into account or not taking into account the additional surface caused by the nanoparticles. If, for example, a resolution of 1 µm is evaluated, the additional surface area caused by nanoparticles of a size of 100 nm, for example, is not taken into account. The inner surface without consideration of the additional surface resulting from the nanoparticles, i.e. the inner surface obtained by the design of the composite as a hierarchical structure alone, is preferably at least twice as large as the outer surface at a resolution of 1 µm, preferably at least five times as large and preferably at least ten times as large.

In connection with this invention, "three-dimensional" means a spatial extension into all three spatial coordinates. The expansion can be essentially uniform in these three directions, so that, for example, a cylindrical shape, a columnar, cuboid or cubic matrix structure is present. However, it is also possible, for example, that the expansion in two directions is larger, but only small in the third direction, so that the three-dimensional structure appears as a plane, e.g. a membrane or layer. Such a surface shape is preferred for the individual structural units of the composite, i.e. they have a length x, a width y and a thickness z, where x and y are each at least twice as large as z, preferably at least three times and more preferably at least five times.

In the context of this invention, the term "biocompatible" means that the scaffold structure and nanoparticles do not induce any toxic, apoptotic, undesirable immunological or other undesirable reaction both in terms of their material composition and their structure in cells, tissues or in an organism, in particular in an experimental animal, and do not interfere or hardly interfere with cellular and molecular processes even after possible internalisation of the nanoparticles or degradation of the nanoparticles and/or scaffold structure.

Composite of Matrix and Nanoparticles

In an embodiment of the present invention, it is intended that the matrix contains nanoparticles which are integrally distributed in the matrix in the scaffold structure. The nanoparticles can be homogeneously distributed in the scaffold structure in the preferred embodiment. However, there may also be a heterogeneous, uneven distribution of nanoparticles in the preferred embodiment. The particle concentration could be present as a gradient in the scaffold structure. If the particles are filled with active ingredient, an active ingredient gradient is also achieved within the scaffold structure. In another preferred embodiment, the nanoparticles are present in the form of at least one layer above and/or below the scaffold structure. In another preferred embodiment, the nanoparticles are present in the form of at least one layer above the scaffold structure.

Preferably the matrix materials and/or the nanoparticles, more preferably the matrix materials and the nanoparticles, are biocompatible and/or biodegradable, more preferably biocompatible and biodegradable.

In a preferred embodiment of the present invention, the mean diameter of the nanoparticles is always smaller than or equal to the mean thickness of the scaffold structure. In another preferred embodiment, the mean diameter of all nanoparticles is always smaller than the mean thickness of the scaffold structure. All nanoparticles, preferably predominantly or completely embedded in the scaffold structure, are preferably available in a preferred design. The preferred ratio of the dimensions of nanoparticles to the thickness of the scaffold structure is 1:1 or less, preferably 1:10 or less, further preferred 1:100 or less, further preferred 1:1000 or less.

Preferably the nanoparticles are contained in a high proportion in the scaffold structure. The nanoparticles can be contained in the composite batch or the composite in a volume fraction of at least 1%, at least 10% or at least 20%. Preferred are volume proportions of 1 to 60%, more preferred 5 to 30%, even more preferred 10 to 30% and most preferred 10 to 20%. In one embodiment, the nanoparticles may be contained in the composite according to the invention in a proportion by weight of at least 1%, at least 10% or at least 20%. Preferred are weight proportions from 1 to 50%, more preferred 5 to 40%, even more preferred 10 to 30% and most preferred 10 to 20%.

The volume and weight percentages given here are based on the dry weight of all components.

The nanoparticles are bound to the resulting matrix by the polymerization of the matrix material. If, for example, the polymer is produced by two-photon absorption, the composite is illuminated in a defined area. In this area the luminous intensity in the focus is strongest and decreases from the inside of the focus to the outside, so that the degree of cross-linking of the polymer also decreases from the inside to the outside. The result is a highly crosslinked polymer on the inside, a weakly crosslinked polymer on the outside and a non-crosslinked polymer on the outside. At this stage, nanoparticles are bound to the strongly crosslinked and weakly crosslinked polymer. After polymerization, a development process takes place in which the chemicals used remove both the weakly crosslinked and the non-crosslinked polymer. Finally, the highly cross-linked polymer with the nanoparticles bound to it remains as a composite. Since nanoparticles are also bound at the interface of strongly and weakly crosslinked polymers, a number of nanoparticles protrude at least partially from the composite.

Preferably the surface roughness is high in the composite according to the invention. In this invention, the surface roughness is determined by atomic force microscopy and given as a value $Z_z$ in nanometers. Preferred values of $Z_z$ are 10 to 10000 nm or 10 to 1000 nm, preferably 30 to 1000 nm, more preferably 50 to 800 nm and most preferably 100 to 800 nm. Alternatively, the surface roughness can be specified as value $Z_q$. Preferred values of $Z_q$ are 1 to 10000 nm, more preferred 1 to 1000 nm, even more preferred 1 to 100 nm and especially preferred 1 to 50 nm or 50 to 100 nm. The surface roughness is determined by the size and number or volume fraction of the nanoparticles in the composite. The preferred combination of average size of nanoparticles and volume fraction of nanoparticles in the composite is 5 to 1000 nm at 3 to 50%, more preferred 10 to 1000 nm at 5 to 50%, even more preferred 30 to 800 nm at 10 to 40%. In the case of larger nanoparticles, the volume fraction is lower, so that it is preferred that the product of the numerical value in nanometers of the mean size of the nanoparticles and the numerical value in percent of the volume fraction of the nanoparticles in the composite is in the range from 100 to 500,000, more preferred 200 to 300,000, even more preferred 300 to 200,000 and most preferred 500 to 15,000.

In this invention, the surface roughness is determined according to ISO4287.

The composite according to the invention is made of at least two components, namely structureable matrix material and nanoparticles. The refractive indices of the components should differ as little as possible. A difference in the refractive indices of the components or a difference in the refractive index of the composite with nanoparticles and without nanoparticles of less than 20%, more preferred less than 10%, still more preferred less than 5% and especially preferred less than 3% at the wavelength at which the structuring is performed is preferred. Another criterion is the absolute difference of the refractive indices at the wavelength at which the structuring is performed. This difference should be less than 0.5 is increasingly preferred to be less than 0.5, less than 0.3, less than 0.2, less than 0.1, less than 0.07, less than 0.05 or less than 0.02.

The composite formulation according to the invention contains a photostructurable material and nanoparticles, wherein the refractive index of the photostructurable material differs by less than 0.5 from the refractive index of the nanoparticles at a wavelength selected from the range of 150 nm to 2000 nm, preferably 150 nm to 1000 nm.

In another embodiment, the composite formulation comprises a photostructurable material and nanoparticles, wherein the refractive index of the nanoparticle composite formulation differs by less than 0.5 from the refractive index of the nanoparticle composite formulation at a wavelength selected from the range of 150 nm to 2000 nm, preferably 150 nm to 1000 nm.

In a preferred embodiment, the composite formulation is selected such that the refractive index of the nanoparticle composite formulation differs by less than 0.5 from the refractive index of the nanoparticle-free composite formulation at a wavelength selected from the range of 150 nm to 1000 nm, and that in the composite obtained after photostructuring, the refractive index of the composite with nanoparticles differs by less than 0.5 from the refractive index of the composite without nanoparticles at a wavelength selected from the range of 150 nm to 1000 nm.

The wavelength value from 150 nm to 2000 nm mentioned in this invention is preferably 150 nm to 1000 nm and more preferably 390 nm to 1000 nm.

This small value of the difference can generally be achieved by the fact that the refractive index of the composite batch with nanoparticles at the wavelength at which the structuring is performed differs by less than 0.5 from the refractive index of the composite batch without nanoparticles. This can be achieved with a difference in refractive index between photostructurable material and nanoparticles of more than 0.5 by the fact that the volume fraction of the photostructurable material is correspondingly larger than the volume fraction of the nanoparticles. The suitable volume fractions can be determined by preliminary testing. In this way, the preferred refractive index differences mentioned above can be achieved. If, for example, the photostructurable material is ORMOCER® with a refractive index of 1.55 and the nanoparticles are magnetite with a refractive index of 2.15, the ratio of the volume fraction of the photostructurable material to the volume fraction of the nanoparticles can be so large that the deviating refractive index of the nanoparticles has little influence and the desired refractive index can be set. Preferably in the example of ORMOCER® and magnetite this ratio is 10/1 and more preferably 99/1.

The small difference of the refractive indices can be achieved in a special case by the fact that the difference of the respective refractive indices of the components, i.e. essentially of the photostructurable material and the nanoparticles, at the wavelength at which the polymerization reaction is carried out, lies within the preferred ranges mentioned. For example, if the refractive indices of the individual components differ by less than 0.5, they can be mixed in the composite batch in any volume ratio to achieve the desired refractive index of less than 0.5.

In this way, the skilled person can adjust the desired difference in refractive index by appropriately selecting the components and the proportions of these components in the composite formulation.

Structuring, i.e. the polymerization reaction, can change the refractive index of the photostructurable material in particular. The refractive index is influenced by the compression of the material by light-induced polymerization reaction and also by the light-induced formation of chemical functionalities with different polarizability. The control parameter here is essentially the material composition, which influences properties such as refractive index via parameters such as functional groups, steric interaction, structure formation and the like. On the other hand, the initiator type and quantity as well as the absorbed dose used play a considerable role.

Due to the polymerization reaction, the difference of the refractive indices of the components in the structured material may differ from the difference of the refractive indices of the components in the composite preparation of structurable material and nanoparticles. Preferably, the components should be selected in such a way that this difference is as small as possible. In the composite according to the invention, the refractive indices of the components preferably differ by less than 0.5, more preferably less than 0.3, less than 0.1 or less than 0.05, even more preferably less than 0.03 and especially preferably less than 0.01 at a wavelength selected from the range of 150 nm to 2000 nm, preferably 150 nm to 1500 nm, even more preferably 150 nm to 1000 nm.

In another preferred embodiment of the present invention, it is intended that the nanoparticles be bonded to the scaffold structure. In the preferred embodiment, the bond is designed in such a way that a change of the medium in which the composite is contained, for example a change of culture medium, does not lead to the detachment of the nanoparticles from the scaffold structure. In the preferred embodiment, the bond is wash stable, i.e. the nanoparticles are not detached from the scaffold structure even if the culture medium is changed and washing steps are carried out with conventional washing media such as buffers.

It is preferred that the nanoparticles are connected to the scaffold structure via electrostatic interactions, in particular through ionic bonding.

In another preferred embodiment of the present invention, it is intended that the nanoparticles are connected to the scaffold structure by UV crosslinking.

The nanoparticles and/or the matrix materials can be functionalised and connected via linking groups for stronger and targeted binding of the nanoparticles to the matrix. These relationship groups can be used as spacers. If these spacers are of different lengths, the effective surface of the composite can be additionally increased. In one embodiment, the integration of the nanoparticles into the matrix and the linkage with nanoparticles can be combined with spacers of different lengths by means of functionalisation.

In another preferred embodiment of the present invention, it is planned that the cell culture system will be used to carry out migration experiments, in particular migration experiments in vitro.

Figures 2A, 2B:
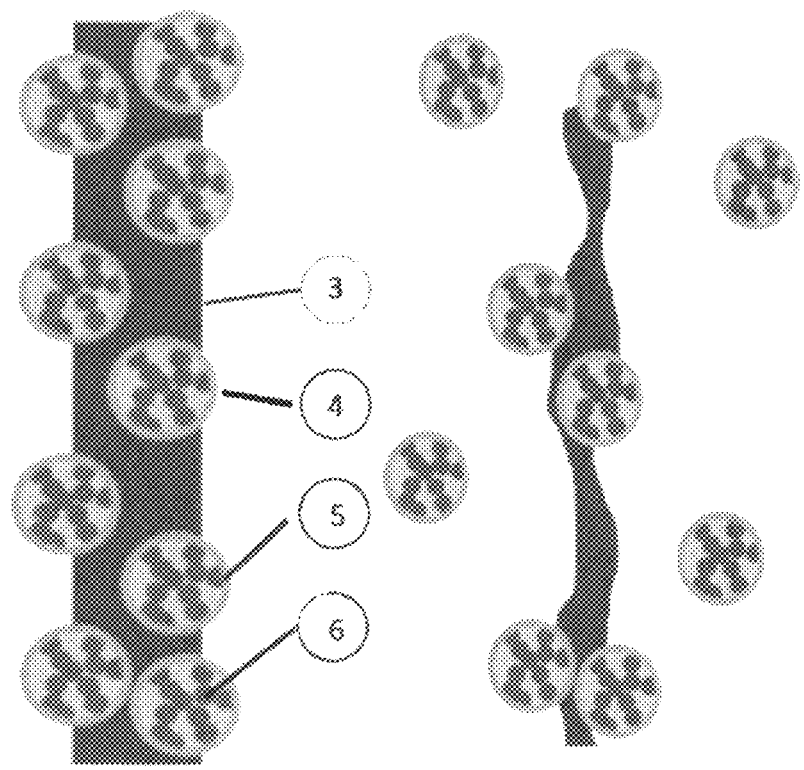
FIG. 2 shows in (a) a schematic representation of a composite with the individual components, whereby the matrix is composed of ORMOCER®. The schematic representation of the release of the drug-charged mesoporous nanoparticles during the biological degradation of the biocompatible matrix is shown in (b).

An example of a composite consists of a photostructurable ORMOCER® matrix with embedded nanoparticles, for example silica nanoparticles (FIG. 2).

Due to the photostructuring capability, the material can be structured using all photostructurable methods such as 3D printing, UV lithography and MPP.

By combining these methods, it is possible to produce any three-dimensionally shaped finely structured scaffolds, e.g. scaffolds, in the centimeter range with a structuring resolution in the submicrometer range (FIG. 1).

The desired structure can, for example, be an extracellular matrix of a biological tissue, so that biological cells can be introduced into the simulated extracellular matrix.

By adding the nanoparticles, it is also possible to achieve an intrinsic surface roughness in the nanometer range without a further process step. This can be varied at will by the diameter of the nanoparticles. For example, it can be adapted to any cell type or the desired cell behavior.

The surface of the nanoparticles can be chemically functionalized to create a suitable chemical interface for the cells or to covalently bind the nanoparticles to the matrix material via corresponding photocrosslinkable groups. The surface of nanoparticles can also be functionalized with bioactive materials or molecules such as collagen, fibronectin, hyaluronic acid, proteins, DNA, RNA, antibodies, integrins, cell receptors, etc. The surface or also the volume of the nanoparticles can be provided with a dye in order to use them as markers or in the released state as sensors.

The matrix can also be intrinsically chemically functionalized.

3-(trimethoxysilyl)propylmethacrylate is an example of a silane that can be a component of ORMOCER®s and serve as surface functionalization of nanoparticles. The nanoparticles can be covalently bonded to the matrix material via such photocrosslinkable groups.

By using silver nanoparticles, it would also be possible to generate antimicrobial surfaces on the 3D structures.

Refractive Index of Different Materials

ORMOCER®s can be used in this invention as structurable matrix materials. These are colorless materials which show no absorption in the visible area. The refractive index depends in particular on the heteroelements (Ti, Zr) used in the ORMOCER®s. For example, increasing the number of Zr—O or Ti—O containing structures in epoxysilane-based ORMOCER®s also increases the refractive index from 1.48 to up to 1.68. Materials based on multiacrylate alkoxysilanes with various spacer groups without heteroelements have been developed to increase the refractive index from 1.52 with linear aliphatic to 1.56 with aromatic or 1.60 with halogenated aromatic spacer groups. To reduce the refractive index of ORMOCER® systems to about 1.45, special multifunctional acrylate systems or fluorinated silanes can be used.

Figure 6:
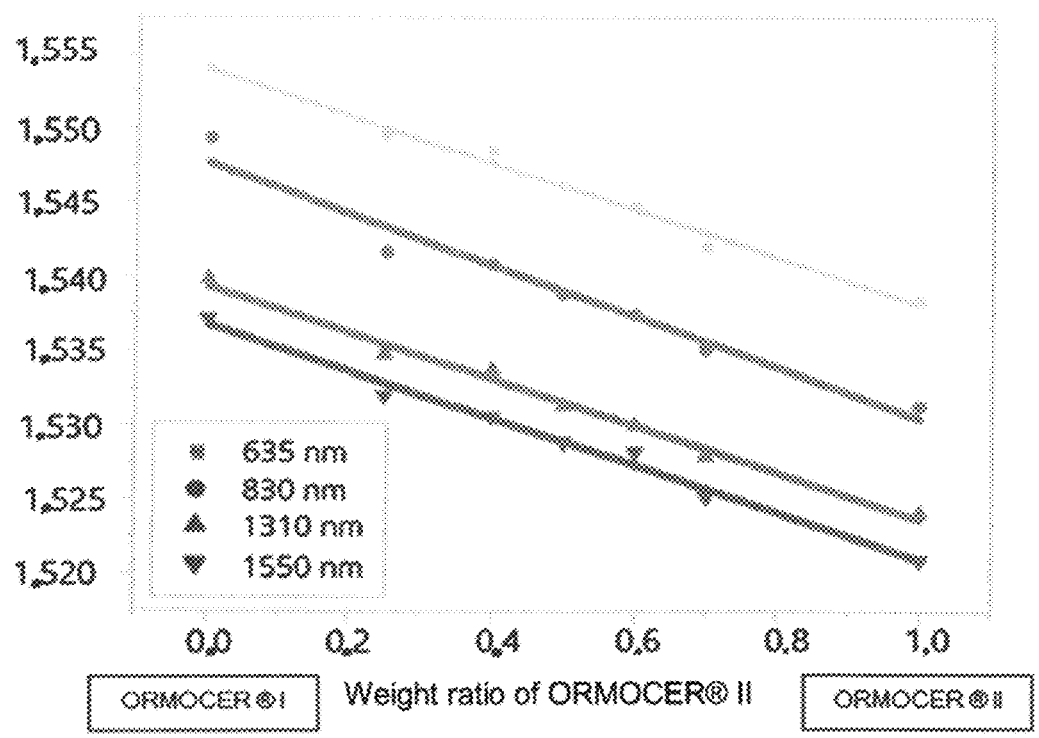
FIG. 6 shows the relationship between the refractive index and the weight proportions of ORMOCER® I and ORMOCER® II in a mixture.

The refractive index of an ORMOCER® mixture can be adjusted very specifically by mixing ORMOCER®s with different refractive indices in a suitable ratio. This is shown in FIG. 6 for ORMOCER® I and ORMOCER®e II.

Examples of precursor molecules of ORMOCER® variants are summarized in Table 1 below. These variants are described in Houbertz R. et al. (2003) "Inorganic-organic hybrid materials for application in optical devices", Thin Solid Films 442, 194-200, in Buestrich R. et al. (2001) "ORMOCER®s for Optical Interconnection Technology" Journal of Sol-Gel Science and Technology 20, 181-186 and in EP 1 196 478 B1.

TABLE 1

| Variant of ORMOCER ® | Precursors |
|---|---|
| ORMOCER ® I | diphenylsilanediol, 3-(trimethoxysilyl)propylmethacrylate (MEMO) |
| ORMOCER ® II | diphenylsilanediol, 3-(trimethoxysilyl)propylmethacrylate (MEMO), trimethoxy(3,3,3-trifluoropropyl)silane |

ORMOCER®s have the optical properties summarized in Table 2.

TABLE 2

| | Refractive index | |
|---|---|---|
| Wavelength | ORMOCER ® I | ORMOCER ® II |
| 635 nm | 1.5527 | 1.5343 |
| 800 nm | 1.543 | 1.532 |
| 1310 nm | 1.539 | 1.524 |
| 1550 nm | 1.537 | 1.521 |

These values are higher than the refractive index of quartz glass (n=1.4585 at 587.6 nm) or PMMA (n=1.492 at 589.3 nm), but lower than the refractive index of polycarbonate (PC) (n=1.590 at 589.3 nm).

Silica has a refractive index of 1.45. Magnetite has a refractive index of 2.4. Particles of $SiO_2$ of size from 260 nm to 680 nm containing from 0 to 6.4% by weight of $Fe_3O_4$ have a refractive index of 1.31 to 1.39.

Inorganic materials have a range of refractive indices, e.g. titanium dioxide (rutile) 3.10 (at 589 nm) and titanium oxide (anatase) 2.52 (at 589 nm), glass 1.45 to 2.14 (at 589 nm), calcium phosphate 1.63, calcium hydrogen phosphate 1.35.

Organic polymers have refractive indices at 589 nm of 1.585 (polycarbonate), 1.55 to 1.63 (epoxy resin), 1.533 (cycloolefin copolymers), 1.534 (polymethacryl methyl imide).

Difference in Refractive Index

In the composite according to the invention, the refractive index of the composite with nanoparticles differs from the refractive index of the composite without nanoparticles by less than 0.5 or by an indicated preferred value at the wavelength at which the polymerization reaction is performed.

The same applies to the composite formulation in the procedure according to the invention.

In one embodiment of the process, the refractive index of the photostructurable material differs from the refractive index of the nanoparticles by less than 0.5 or a said preferred value at the wavelength of the irradiation carried out in step (ii).

The photostructurable material can be a single material or a mixture of materials with a certain refractive index.

Accordingly, an expression such as "nanoparticles having a refractive index of x" may mean a single species of nanoparticles or a mixture of nanoparticles of different composition, size, refractive index and the like, the mixture having the refractive index x.

The difference between the refractive index of the composite with nanoparticles and the refractive index of the composite without nanoparticles in the invented composite can be determined in different ways.

If the nanoparticles can be separated from the composite, e.g. by washing, the refractive index can be measured before and after separation.

If the nanoparticles cannot be separated non-destructively from the composite, it is possible to determine the composition and structure of the nanoparticles spectrometrically or in combination with other analytical methods and to produce the desired nanoparticles with the analytical data. The measured refractive index of these nanoparticles can then be subtracted from the refractive index of the composite. In the present invention, the determined value is then regarded as the difference between the refractive index of the composite with nanoparticles and the refractive index of the composite without nanoparticles.

Accordingly, it would be possible to determine the structure and composition of the matrix, to produce the matrix and to determine its refractive index. The refractive index difference of the composite with nanoparticles and without nanoparticles could then also be determined from the measured data obtained.

Preparation of Matrix Structures

Stereolithography offers a possibility for the fabrication of finely structured scaffolds or highly complex structures. In this technique, a chemical reaction, namely photopolymerization, is initiated by electromagnetic radiation. The material to be structured or the material formulation to be structured must therefore fulfil the requirement of being able to react with light. As a result, a phase transition from liquid to solid takes place in the exposed areas. In the subsequent development step, only the remaining liquid material is dissolved away. With the help of a laser beam, structures can be generated layer by layer. The advantages of this method are that highly organized three-dimensional scaffolds with defined porosity, pore size and interconnectivity of the pores can be produced with high reproducibility and this is possible with only a few process steps.

A special case of stereolithography, namely two-photon polymerization (2PP), offers good resolution. With this technique ultrafine structures can be generated at high resolution. It is based on the simultaneous absorption of two photons (two photon absorption, TPA), which triggers the decay of the initiator molecules and thus the subsequent chemical reaction between the generated radicals and the monomers. Due to the simultaneous absorption of two photons, very high light intensities are required for excitation, which can be realized by ultrashort laser pulses. The rate of two-photon absorption depends non-linearly on the intensity.

As a result, polymerization takes place only in a spatially narrow area around the laser focus within the liquid to be solidified, whereby resolutions of <100 nm can also be achieved. If the focus is moved through the material, three-dimensional microstructures are created in the exposed areas in one process step. This allows a relatively small space within the liquid to be solidified to be controlled with relatively good accuracy, which is solidified by the input energy. The production of the moulded body can therefore take place within a corresponding liquid, no longer (only) on its surface.

In a preferred embodiment of the invention, the liquid is solidified by irradiation with femtosecond laser pulses. Common polymerizable materials can be exposed to ultrashort laser pulses with high peak energy, e.g. Ti:sapphire femtosecond laser pulses. These are irradiated with wavelengths in the range of about 800 nm into the resins to be solidified.

Ti sapphire lasers can preferably be used as suitable lasers (either with the fundamental wavelength of 780 nm or, depending on the absorption behavior of the liquid to be hardened, with the second harmonic at 390 nm); other NIR lasers (e.g. with emitted wavelengths of 800 nm to about 1500 nm) are also suitable. But other laser irradiation is also possible if the light source used can irradiate the liquid with an intensity suitable for multiphoton excitation. This property is offered in particular by short pulse lasers with moderate average power. The material to be cured must be transparent for the laser wavelength used. If, for example, the material to be solidified could be polymerised with one photon at 390 nm, any wavelength of 400 nm or more could be used for two- or multi-photon polymerisation; depending on the resin, 500-1000 nm are the most suitable due to the transparency conditions. If longer wavelengths are used, polymerization can also be initialized by n-photon absorption, where n is greater than 2.

In particular, the use of femtosecond lasers as radiation sources results in bodies/layers with high lithographic resolution. The type and duration of irradiation also allow the degree of crosslinking to be varied so that different physical properties (e.g. degradability at different rates) can be achieved with one and the same material if required. The degree of cross-linking can also be varied within a scaffold structure. This can either be done at certain points or as a gradient. With this process not only three-dimensional structures on substrates (carrier materials) can be produced, but also three-dimensional self-supporting bodies can be produced completely out of the volume.

The inventive process makes it possible to produce three-dimensional shaped bodies with a continuous porous network within the shaped body over a large area by light-induced cross-linking processes, in particular by multi-photon absorption technology over a wide wavelength range using a wide variety of laser and optical systems in-situ. In particular, the process described can be used to produce large structures and shaped bodies with a size down to the cm range.

By combining different photostructuring methods, desired hierarchical structures can be created. In this way, a hierarchical structure from the centimetre to the nanometre range can be adapted at will. For example, superstructures in the centimetre range can be produced by a rapid prototyping process and substructures by multi-photon absorption (MPA).

The pore structures are selected as desired, e.g. depending on the cell types to be applied to the carrier matrix.

In contrast to stereolithographic methods, which solidify an object layer by layer in a bath of a liquid solidifiable by the action of radiation while moving the object further into the bath, a three-dimensional body to be produced by means of femtosecond laser irradiation is produced in only one working step on a surface or in volume.

The two- or multi-photon polymerization of the organic residue polymerizable by two-photon or multi-photon polymerization can take place via one or more groups that can be polymerized radically. Non-aromatic C=C double bonds such as allyl or vinyl groups are suitable as radical polymerizable groups, but double bonds accessible to Michael addition are particularly preferred.

Examples of photostructurable matrix materials are inorganically condensable silanes and their condensates and/or polymers. These silanes contain one or more substituents or groups bonded to the silicon via oxygen and having ester bonds or, if desired, also having ether and/or thioether bonds, as well as organically polymerizable units such as C=C double bonds or ring-opening systems, e.g. epoxy groups. The silanes can be condensed inorganically and/or polymerized organically via the C=C double bonds. Such an organic polymerization can, for example, be carried out with the aid of 2-photon polymerization (2PP), so that structured, essentially monomer-free materials can be obtained. By varying the proportion of inorganically crosslinkable units and/or organically polymerizable units, the mechanical properties of the hybrid polymers produced from the silanes can be specifically adjusted to resemble those of natural, soft or hard tissue. These hybrid polymers are particularly suitable for the production of scaffolds.

The well-known ORMOCER® hybrid materials can be solidified both by organic polymerization of C=C double bonds and by inorganic crosslinking reactions (Si—O—Si bridge formation), whereby the presence of organically polymerizable C=C double bonds permits spatial structuring during polymerization.

A desired three-dimensional matrix structure is produced in an embodiment of the invention.

In a first step of the process to produce a desired structure, data are provided that describe the desired structural structure. The data describes the geometric shape of the structure.

In a further step of the process, a precursor of a biopolymer is provided. The precursor is a starting material in the sense of a precursor of the biopolymer, for example in the form of a monomer. The biopolymer is, for example, a biocompatible and/or biodegradable polymer.

The precursor is locally irradiated with electromagnetic radiation, whereby the irradiation, in particular the selection of the areas to be irradiated, is carried out according to the structural structure described by the data. This means that exactly those coherent subsets of the plane or space are irradiated which are defined by the data. The electromagnetic radiation can, for example, be formed by a focused light or by a laser beam.

In accordance with the invention, the electromagnetic radiation is measured in such a way that in the irradiated regions of the precursor a two- or multiphoton absorption takes place, by means of which the precursor in the irradiated regions is polymerized to the biopolymer, so that it at least partially solidifies there. Since the irradiation of the precursor is locally targeted according to the structural structure described by the data, the polymer formed is formed with the desired structure.

In another embodiment of the process, parts of the precursor that are not polymerized after irradiation are washed out. Cavities, among other things, are emptied by the rinsing out.

Nanoparticles

In the context of this invention, nanoparticles are defined as particles with a diameter of 1 to 10000 nm, preferably 1 to 1000 nm. Such nanoparticles can be composed of different materials, for example inorganic or organic substances. In their preferred embodiment, their surfaces may contain chemically reactive functional groups that form affine bonds, i.e. covalent and/or non-covalent bonds, with complementary functional groups of active substances to be bound, thus enabling the active substances to fix stably to their surfaces. The invention at hand provides, in another preferred embodiment, that the nanoparticles can also form bonds with the scaffold structure. Such bonds are preferably electrostatic interactions or covalent bonds.

In a preferred embodiment, the nanoparticles have an average diameter from 1 to 10000, preferably from 5 to 1000 nm, preferably from 20 nm to 900 nm, preferably from 30 to 600 nm. In another preferred design, the nanoparticles have an average diameter of 30 to 500 nm.

The term "mean size" or "mean diameter" of nanoparticles used in this invention is the median of the particle diameter $D_{n,50}$ in relation to the number of particles.

In a further embodiment it is planned that the nanoparticles are composed of inorganic substances such as gold or other precious metals or metals or metal oxides, calcium phosphate and calcium hydrogen phosphate or other mixed phosphates, silicon-based oxidic materials such as silicates, silicon oxides such as silicon dioxide. The nanoparticles can also be DynaBeads in preferred embodiments.

In one embodiment, the nanoparticles are mesoporous silica nanoparticles. In a further embodiment it is a matter of Janus particles.

In a preferred embodiment, the nanoparticles are provided with a fluorescent dye in volume or on the surface. This allows the scaffold structure to be imaged through a fluorescence microscope. In the case of a biodegradable matrix, the released nanoparticles can serve as markers or sensors. For example, the degree of scaffold degradation can be easily detected by fluorescence microscopy. If the nanoparticles are absorbed by cells, they can be used as cell-internal sensors. If the dyes are additionally coupled to antibodies, the nanoparticles can only be detected via the fluorescence signal after successful antigen binding and thus numerous biological processes can be investigated or detected.

In another embodiment, the nanoparticles consist of magnetic, piezoelectric or other magnetic/electroactive materials such as iron, magnetite, barium titanate or polyvinylidene fluoride to create structures that can be activated by magnetic or electric fields.

In a preferred embodiment it is intended that the nanoparticles are composed of organic materials, in particular organic polymers. The nanoparticles can preferably be produced by emulsion polymerisation.

Nanoparticles composed of biodegradable polymers are preferably used in the composite according to the invention. Another preferred method is to use nanoparticles with a diameter of 50 nm and a biodegradable matrix.

In another preferred embodiment, it is intended that the nanoparticles should consist of polylactides (PLA), poly(lactid-co-glycolid)en (PLGA), polycaprolactones (PCL), polyglycolides, di- and tri-block polymers, for example. PCL/PGA di-block systems, polyorthoesters (POE), polyanhydrides, polyhydroxyalkanoates (PHA), polypyrroles (PPy), polypropylene carbonate, polyethylene carbonate, polyalkylcyanonitrile or polyethylene glycol.

The preferred option is for the nanoparticles to have polymers with different molecular weights and variable polarity depending on the desired release profile of the active ingredient. The selection of the material to be used for the construction of the nanoparticle can be made in the preferred embodiment according to the mode and kinetics in which the active substance is to be released.

In another preferred embodiment of the present invention, it is envisaged that the nanoparticles have been functionalised by coupling with functional groups. In a particularly preferred embodiment, it is intended that the nanoparticles themselves have functional groups on their surface.

The term "nanoparticles" used in this invention means a single type of nanoparticle or a mixture of different nanoparticles. The difference of the nanoparticles in the mixture is at least one selected from the group consisting of the composition of the nanoparticles, the size of the nanoparticles and the refractive index of the nanoparticles. For example, this means that an expression such as "nanoparticles with a refractive index of x" may also mean a mixture of nanoparticles of different composition, size, refractive index and the like, the mixture having the refractive index x.

EXAMPLES

This invention is further illustrated by the following examples.

Figure 7:
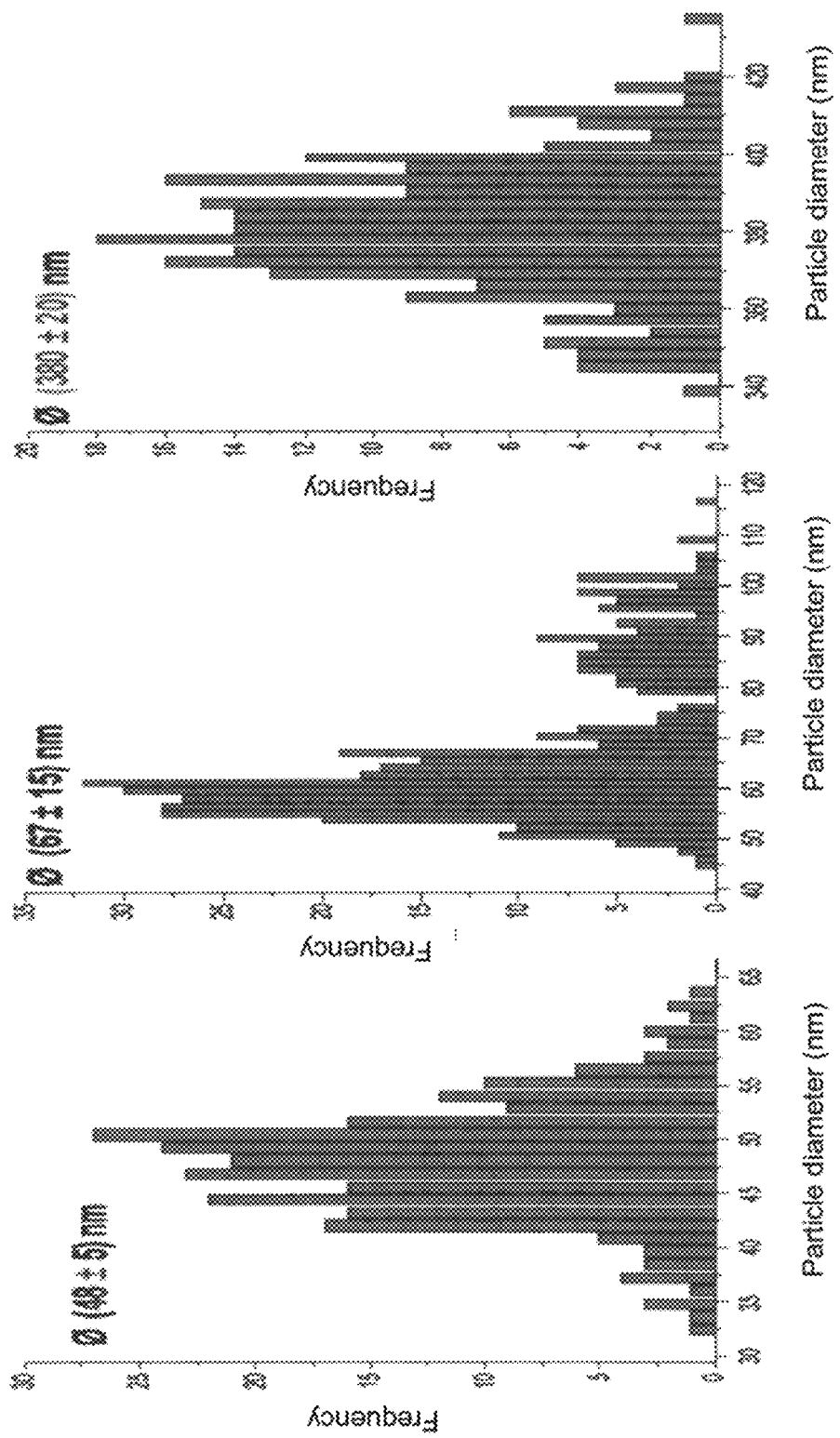
FIG. 7 shows the number-weighted particle size distribution of the silica nanoparticles used in the examples, which were determined by scanning electron microscopy.

For the following example, the matrix material used was the ORMOCER® I from the ORMOCER® family described above, which shows very good biocompatibility. For the production of ORMOCER® I, in addition to the formulation disclosed in Buestrich et al. (2001), 2 wt. % Irgacure 369 was added as a photoinitiator (cf. Houbertz et al. (2003)). Silica nanoparticles (SNP) were used as fillers, which were produced by the Stöber process. The particles were stirred into the matrix and homogenized in an ultrasonic bath. In order to demonstrate the influence of surface roughness on cell behavior, composite preparations of ORMOCER® I and SNP with a filling degree of up to 20% by volume were prepared according to the methods described above (Table 3). The diameter of the SNP was varied and the particle size distribution determined by scanning electron microscopy (FIG. 7).

The results are summarised in Table 3 below.

different photostructuring processes within a sample and thus to realize dimensions in the centimeter range (3D printing), millimeter to micrometer range (lithography) and submicrometer range (MPP). This is supplemented by nanoparticles down to the nanometer range. For this example, lines (length: 1 mm, width: 100 µm, height 15 µm) made of ORMOCER® I were lithographically structured on a cover glass. Subsequently, the lines were coated with OC-D and crossed by MPP into the interspace (line width: 6 µm, lattice period: 15 µm). A pulsed 80 MHz Ti:Sapphire laser (Coherent Ultra II) at a wavelength of 705 nm was used for structuring and focused into the material with an oil immersion objective (Nikon, NA=1.45) at a power of 6 mW and the sample was moved at a speed of 1 mm/s. The laser was then moved at a speed of 1 mm/s. The sample was then subjected to a laser beam with an oil immersion lens (Nikon, NA=1.45).

Figure 8:
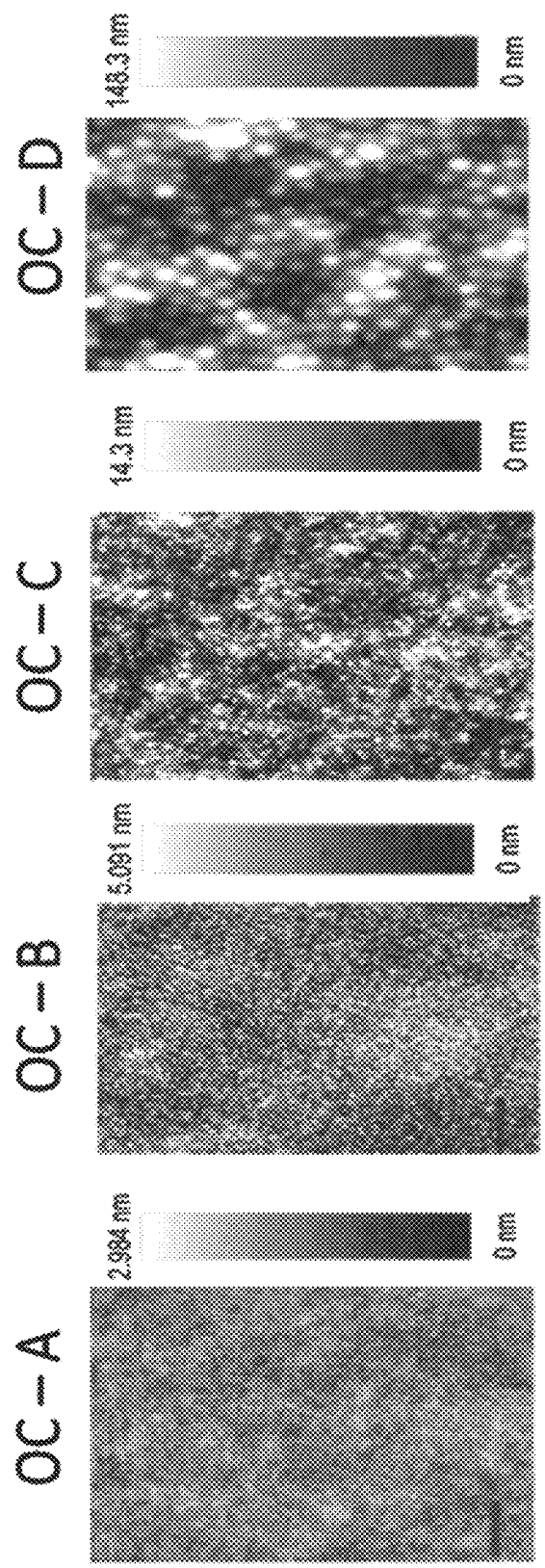
FIG. 8 shows scanning force microscopic images of the doctored surfaces, without filler (OC-A) and filled with increasing particle diameter (OC-B to OC-D). The scale corresponds to 2 µm.

Using the squeegee method, flat layers with a thickness of approx. 10 µm were produced from the composites under clean room conditions and cross-linked by UV irradiation. The surface roughness was determined by atomic force microscopy and compared with that of an ORMOCER® I layer without filler (FIG. 8). This shows a roughness of only Zz=(6.9±2.3) nm which could be increased to Zz=(316±45) nm by adding the nanoparticles (Table 3).

On the layers described above fluorescence-labelled, freeGFP expressing *D. dictyostelium* (HG1694) cells were cultured and a migration analysis (according to Gorelashvili et. al, Amoeboid migration mode adaption in quasi-3D

TABLE 3

Composition of the manufactured ORMOCER ® I-SNP composites and the results of the mean particle diameter and surface roughness of the doctored layers. The specified error results from the standard deviation of the measurements.

| Formulation | OC-A | OC-B | OC-C | OC-D | OC-E |
|---|---|---|---|---|---|
| Matrix Material | ORMOCER ® I | ORMOCER ® I | ORMOCER ® I | ORMOCER ® I | ORMOCER ® I |
| | | Silica nanoparticles | | | |
| Filling degree [vol.-%] | 0 | 20 | 20 | 20 | 10 |
| $D_{n, 50}$ (nm) | — | 48 ± 5 | 67 ± 15 | 380 ± 20 | 67 ± 15 |
| | | Squeegee layers | | | |
| Zq (nm) | 0.8 ± 0.1 | 1.5 ± 0.1 | 4.2 ± 0.1 | 38 ± 1 | |
| Zz (nm) | 6.9 ± 2.3 | 25 ± 12 | 41 ± 1 | 316 ± 45 | |

Figure 3:
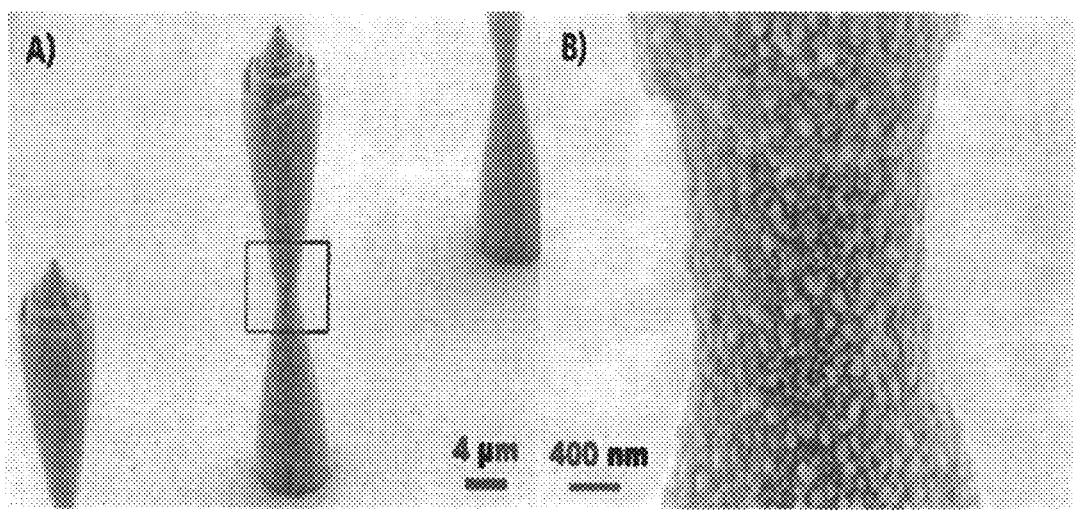
FIG. 3A) shows a SEM image of a 3D structure made of composite OC-E using 2PP. The scale corresponds to 4 µm.
FIG. 3B) shows a zoom shot of the section from FIG. 3A) showing the nanoparticles and the corresponding surface roughness of the 3D structure. The scale corresponds to 400 nm.

FIG. 3 shows an example of a 3D structure from the OC-E formulation, which was produced using 2PP. For structuring a pulsed 80 MHz Ti:Sapphire laser (Coherent Ultra II) at a wavelength of 705 nm was used. FIG. 3B shows an excerpt from FIG. 3A and illustrates the roughness of the surface on the 3D structure.

Figure 4:
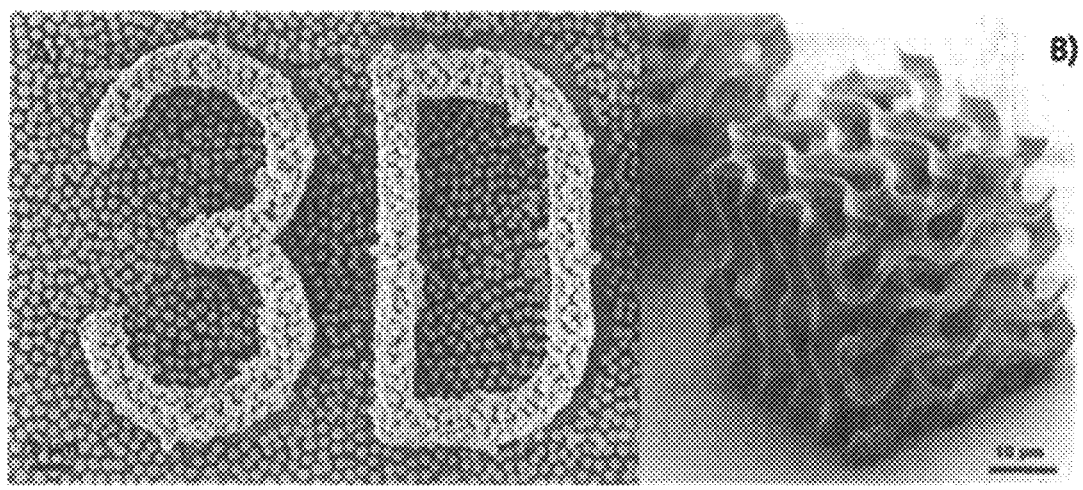
FIG. 4 shows a SEM image of 3D structures produced using the MPP process. OC-D was used for the structure in A); the scale corresponds to 2 µm. OC-B was used for the structure in B); the scale corresponds to 10 µm.

Complex 3D structures with a high resolution could also be produced from the composites with a filler content of 20% by volume. Here, both the classical method, in which the sample is moved laterally and the objective is moved axially mechanically (FIG. 4A), and the scanner method, in which the focus is deflected laterally via mirrors with galvanometer drive and only the objective is moved mechanically in the axial direction (FIG. 4B), can be used. For the gyroid structure in FIG. 4B, the laser T-pulse of the amplitude brand (wavelength after frequency doubling: 515 nm) was used with a scanner unit from the manufacturer Lightfab.

Figure 5:
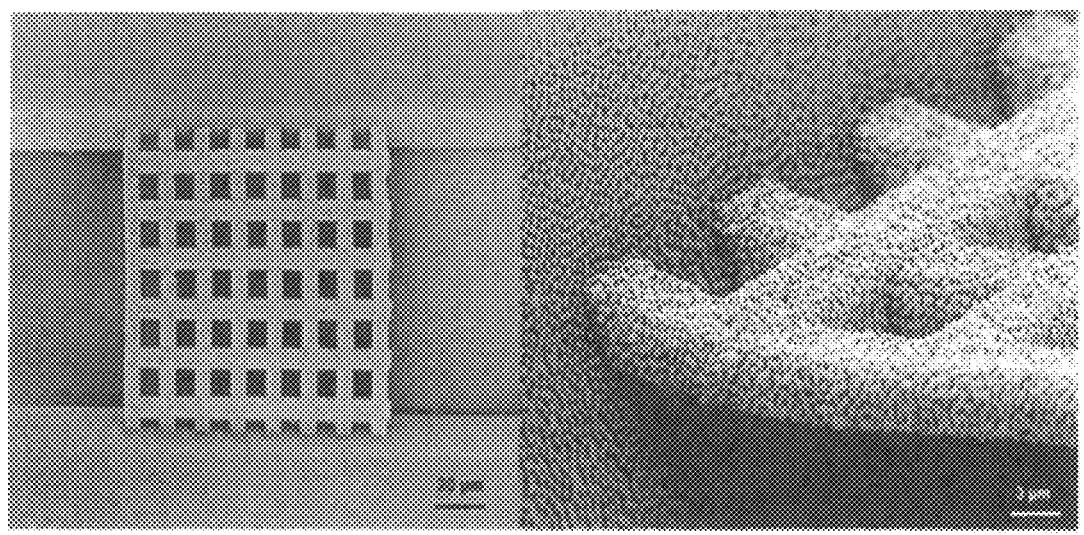
FIG. 5 shows a SEM image of an OC-D composite structure fabricated using MPP, placed between two ORMOCER® lithographically fabricated cuboids. A) Top view; B) 60° tilted image showing the transition between lithographic and MPP structures. The scale in A) corresponds to 20 µm, the scale in B) corresponds to 3 µm.
Figure 9:
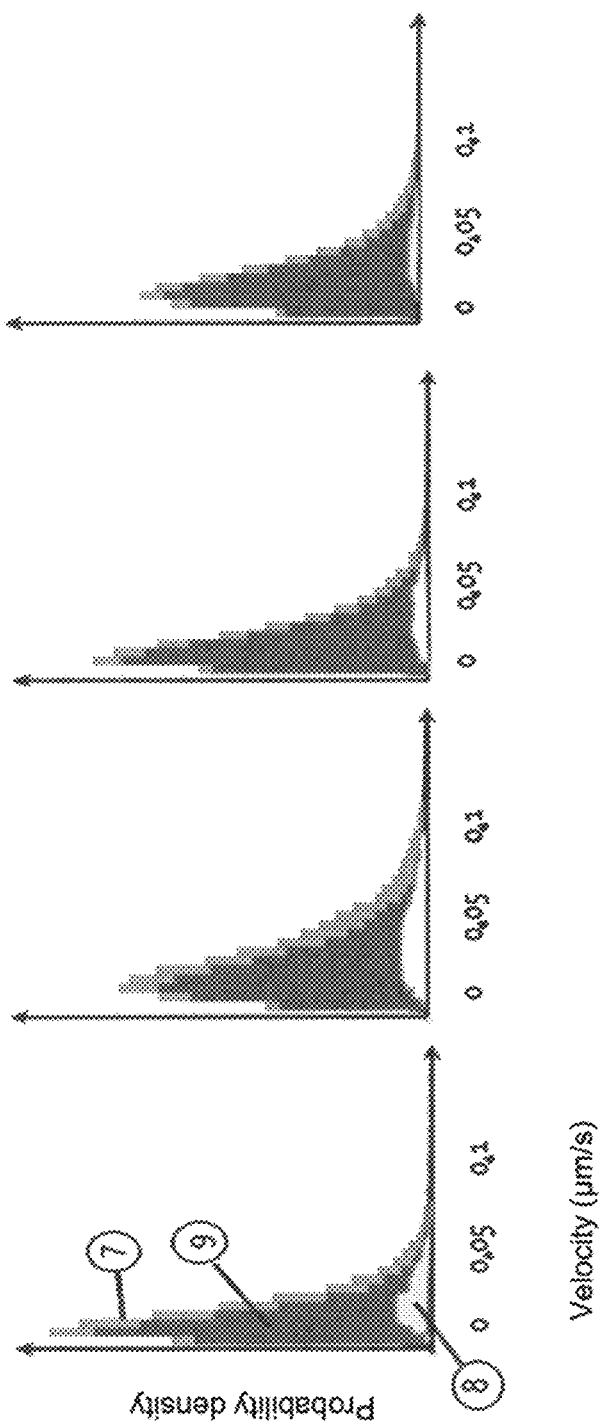
FIG. 9 shows a migration analysis with cells of *D. dictyostelium* on doctored surfaces, without filler (OC-A) and filled with increasing particle diameter (OC-B to OC-D). Active migration phases are shown brighter and passive migration phases darker.

FIG. 5 illustrates the advantage of the hierarchical structuring of the composite, whereby it is possible to combine spatial density gradients of varying lattice geometry, New Journal of Physics, 16, 2014) was performed by time-lapse fluorescence microscopy. It was shown that with increasing surface roughness, the active migration phases decrease and the average speed of cell migration increases, so that the migration behavior can be specifically influenced (FIG. 9).

In a further experiment it was shown that a high-quality structuring of composites is possible with a high refractive index difference of the components, if a component is only contained in a low concentration in the composite batch. Composites with a high refractive index difference of the components are produced, for example, if further material properties are to be introduced into a structure by the selection of nanoparticles. For example, silver nanoparticles are used to create antibacterial surfaces, which is a great advantage for implants. Barium titanate particles make it possible to produce actuator structures in order to exert mechanical stimuli on cells. By using magnetite particles, moving structures can be generated using external magnetic fields, or the magnetite particles can be used as contrast agents for MRI or MPI to monitor the structures.

Figure 10:
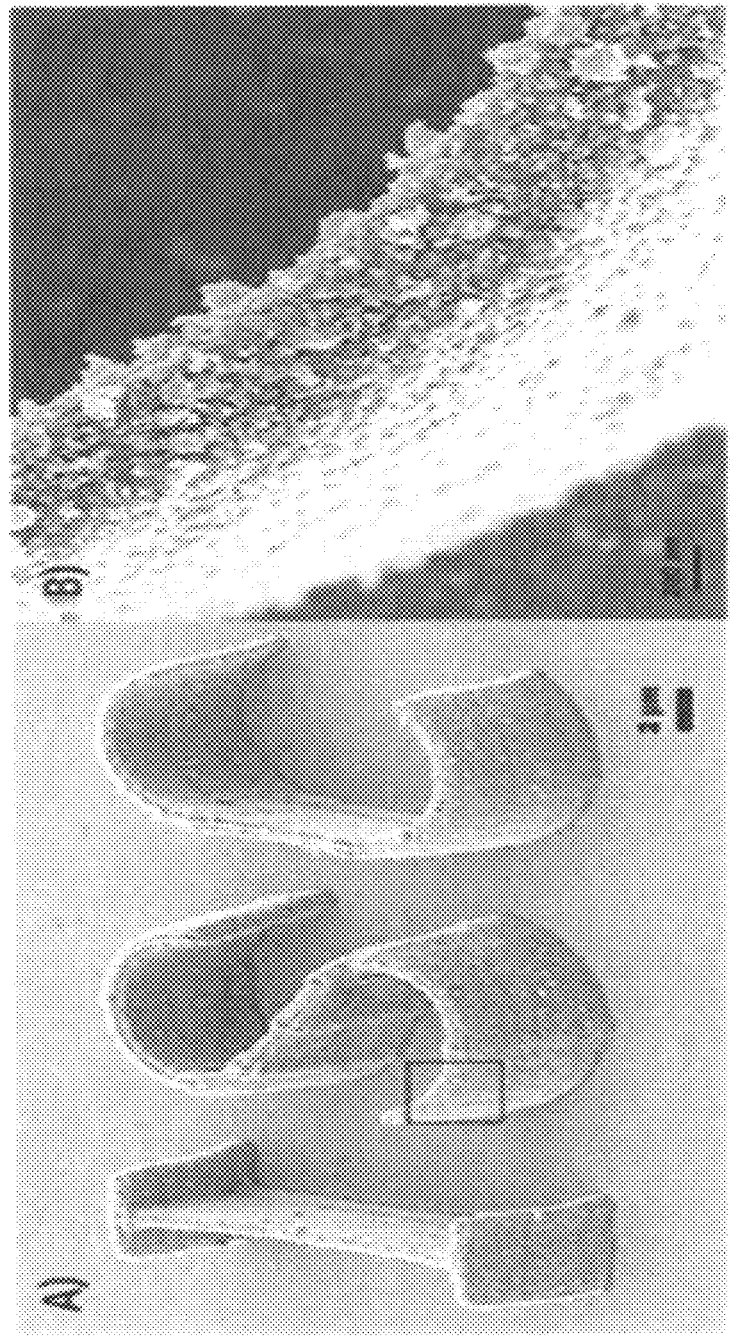
FIG. 10A) shows a SEM image of a 3D structure made from a composite of superparamagnetic magnetite particles and ORMOCER® using MPP.
FIG. 10B) shows the magnification of the section marked in FIG. 10A). The scale in A) corresponds to 2 µm, the scale in B) corresponds to 200 nm.

Although the high refractive index difference of ORMOCER® I (1.55 at 589 nm) and magnetite (2.15 at 589 nm), for example, impairs the quality of the focus and thus the resolution of the structuring, the quality can be compensated to a certain degree by adjusting the fill level, laser wavelength or laser power. Such adjustments are necessary if non-transparent and highly absorbent materials are to be structured. In the present case, a composite of ORMOCER® I and superparamagnetic magnetite nanoparticles (particle size 10-15 nm) with a filling degree of 1% by volume was prepared according to the procedure described above. A pulsed 80 MHz Ti:Sapphire laser (Coherent Ultra II) at a wavelength of 705 nm was used for structuring and focused into the material with an oil immersion objective (Nikon, NA=1.45) at a power of 3.75 mW and the sample was moved at a speed of 0.1 mm/s. The laser was then used for the structuring. Due to the adjustments mentioned above, in particular due to the low filling level, it was also possible to obtain a detailed structuring in this case (cf. FIG. 10).

Cytotoxicity of the Composites Used

The composites from Table 3, consisting of silica and ORMOCER® I, were used for experiments with mammalian cells and tested for cytotoxicity according to ISO 10993 with an extract test.

Figure 11:
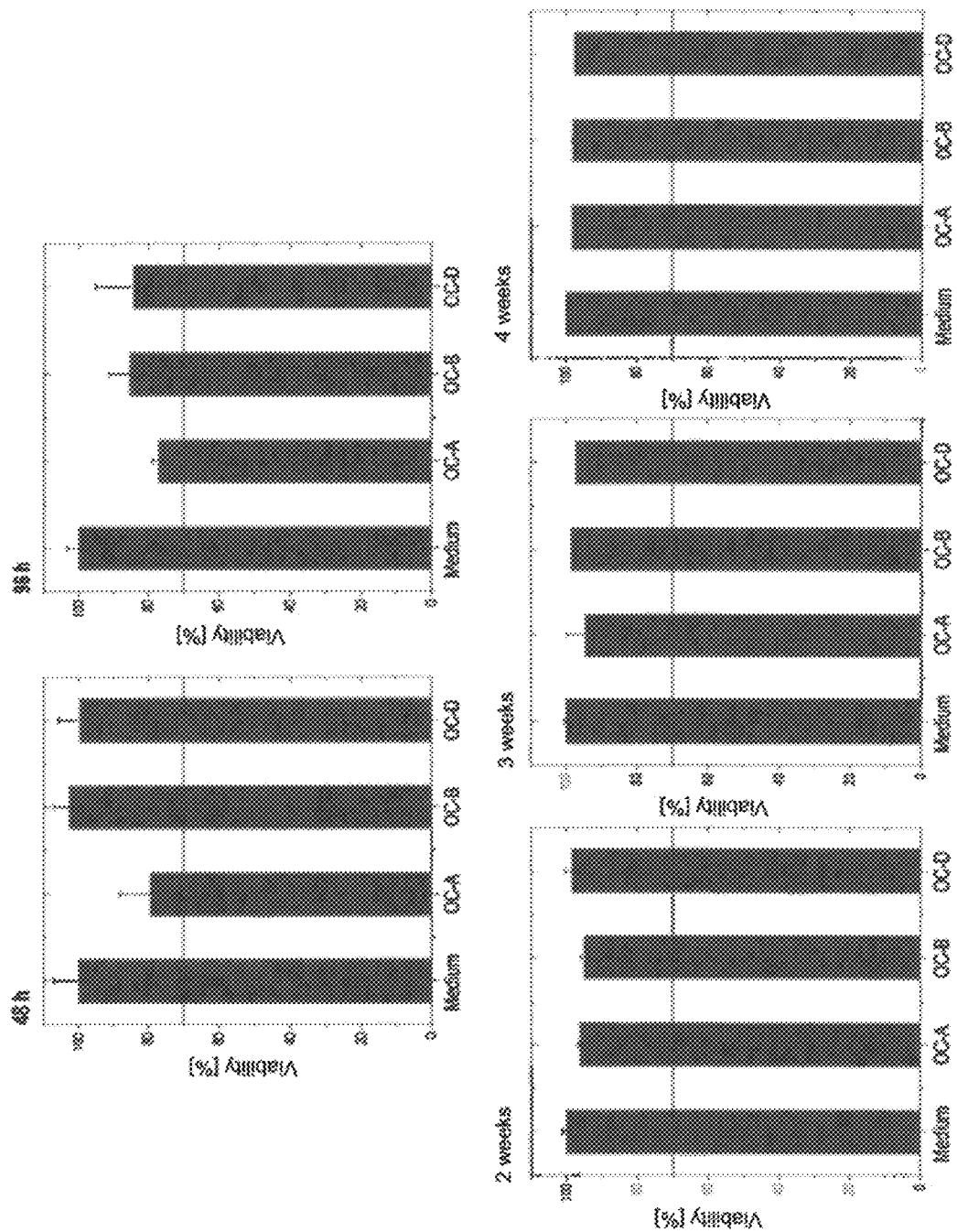
FIG. 11: Cell viability of murine L929 fibroblasts cultured in an extract for 48 hours using the WST test. The extract was prepared by incubating the samples to be examined in DMEM medium for different periods of time. Incubated medium without sample serves as reference and corresponds to a viability of 100%.

For this purpose, discs with a thickness of 120 µm were produced from OC-A and the composites OC-B and OC-D. The OC-B and OC-D were used for the fabrication of the discs. These were cultivated for different periods in DMEM medium at 37° C., steam saturated and with 5% $CO_2$ enriched atmosphere on a shaker. Subsequently, murine L929 fibroblasts were cultured in the extract for 48 hours and viability was determined by WST-1 assay using 4-[3-(4-iodophenyl)-2-(4-nitrophenyl)-2H-5-tetrazolio]-1,3-benzene disulfonate. As a negative control, cells were cultured in a DMEM medium without composite samples, and their cell viability yielded the 100% reference value. The results for different extraction times are shown in FIG. 11. The red line at a viability of 70% indicates the limit above which a test substance can be classified as non-cytotoxic according to ISO 10993. All three materials tested passed this criterion for all investigated incubation times, which is a strong indication of high biocompatibility.

Autoclavability of Composite Structures Produced with TPA

The autoclavability of a composite was investigated, i.e. the treatment with steam at 121° C. at 1 bar overpressure for 20 min. was investigated.

Figure 12:
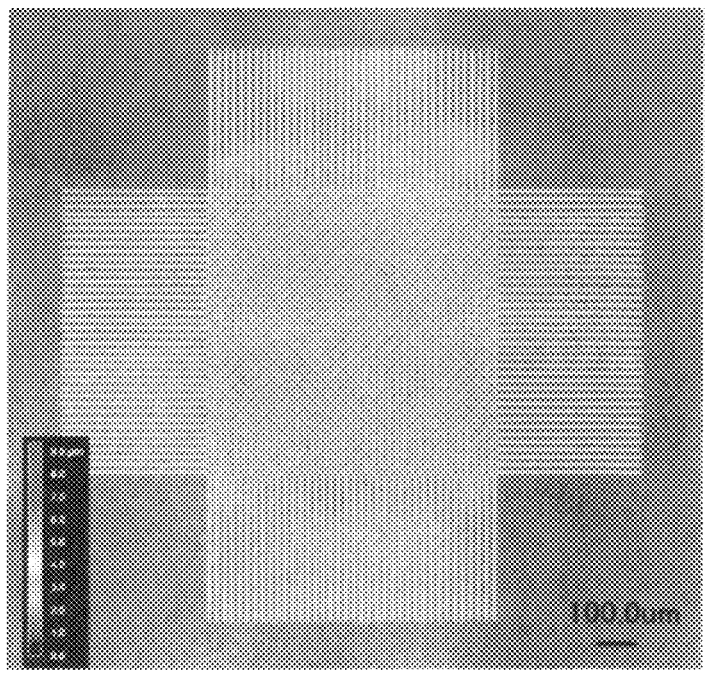
FIG. 12: Scanning laser microscope images of the crossed line field design for investigations of autoclavability and cell morphology using OC-D as an example. The lines have a square cross-section of 5×5 µm and a total length of 1.5 mm. (A): Supervision of the overall structure. (B): 3D view of a section of the area with crossed lines.
Figure 12:
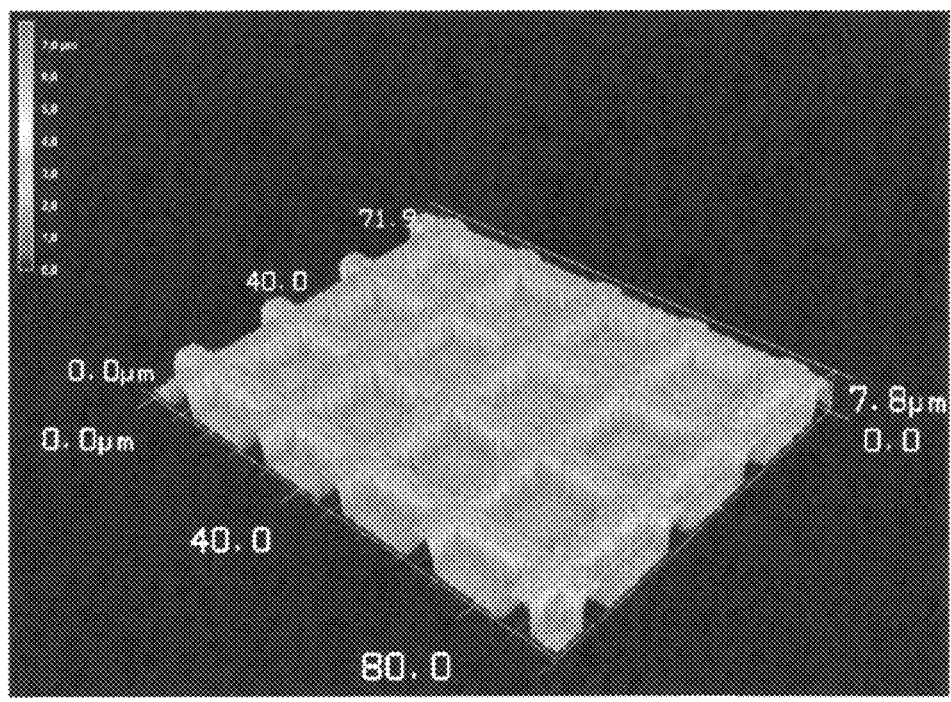
Figure 13:
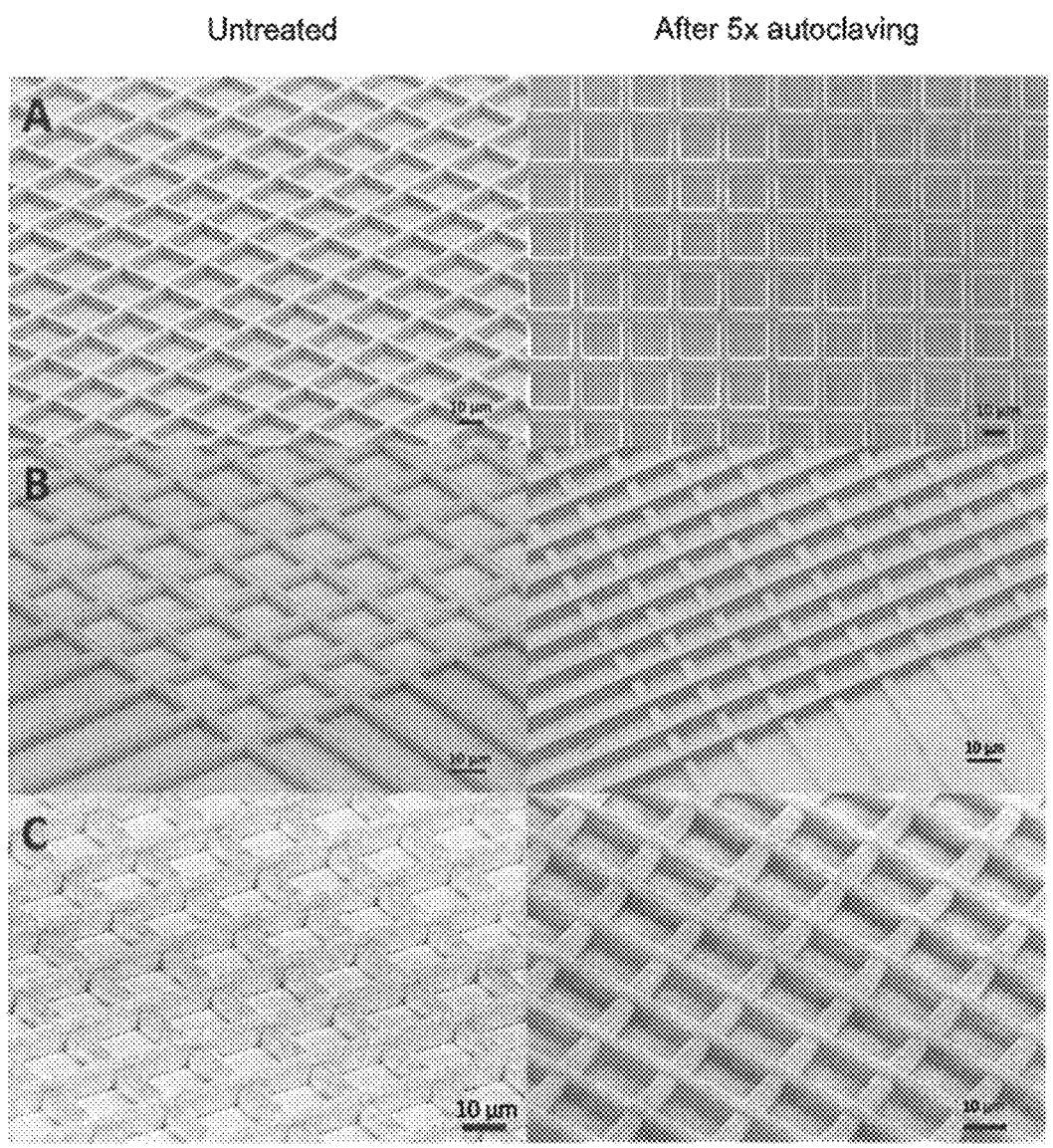
FIG. 13: Scanning electron microscope images of crossed line structures before autoclaving (A) and after five times autoclaving (B) for different composite systems: A) OC-A, B) OC-B, C) OC-D.

For this purpose, an approx. 10 µm thick composite layer was first applied to a glass substrate, cross-linked by UV and then a 1.5×1.5 mm grid structure of crossed lines with a height and width of 5 µm was applied using TPA (FIG. 12). These samples were autoclaved five times (Systec V-65, Systec GmbH, Linden) and then examined by scanning electron microscopy (FIG. 13). No structural or topographical changes were observed.

Morphology Analysis of 3T3 Cells on Composite Structures Produced by TPA

3T3 cells were seeded on the structures shown in FIG. 12 and examined after 48 hours incubation with a confocal fluorescence microscope.

Figure 14:
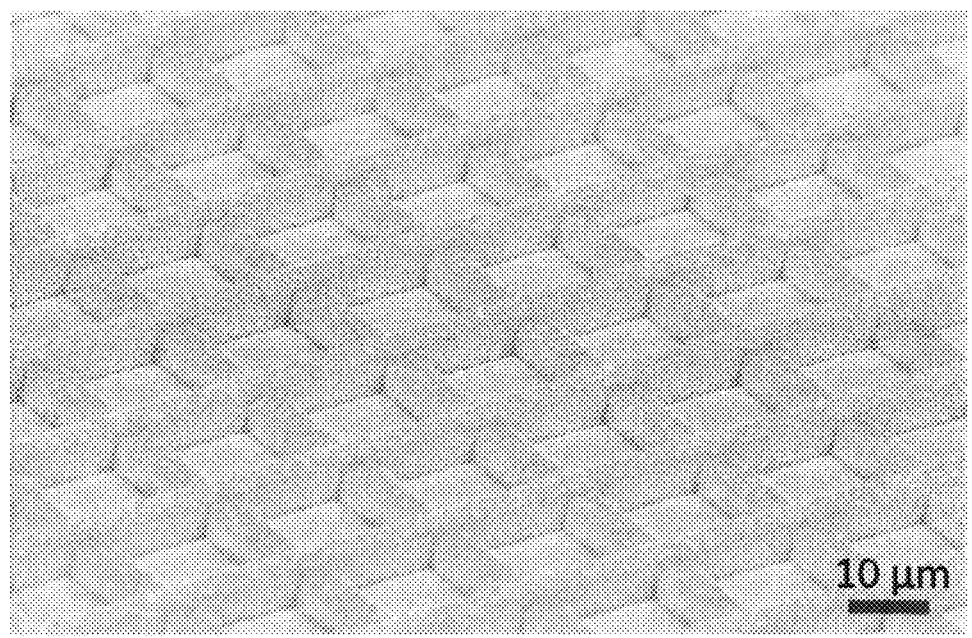
FIG. 14: (A): Scanning electron microscope image of the sample area with crossed lines using OC-D as an example. (B): 3D fluorescence microscope image of 3T3 mouse fibroblasts after 48 hours of incubation on the structure.
Figure 14:
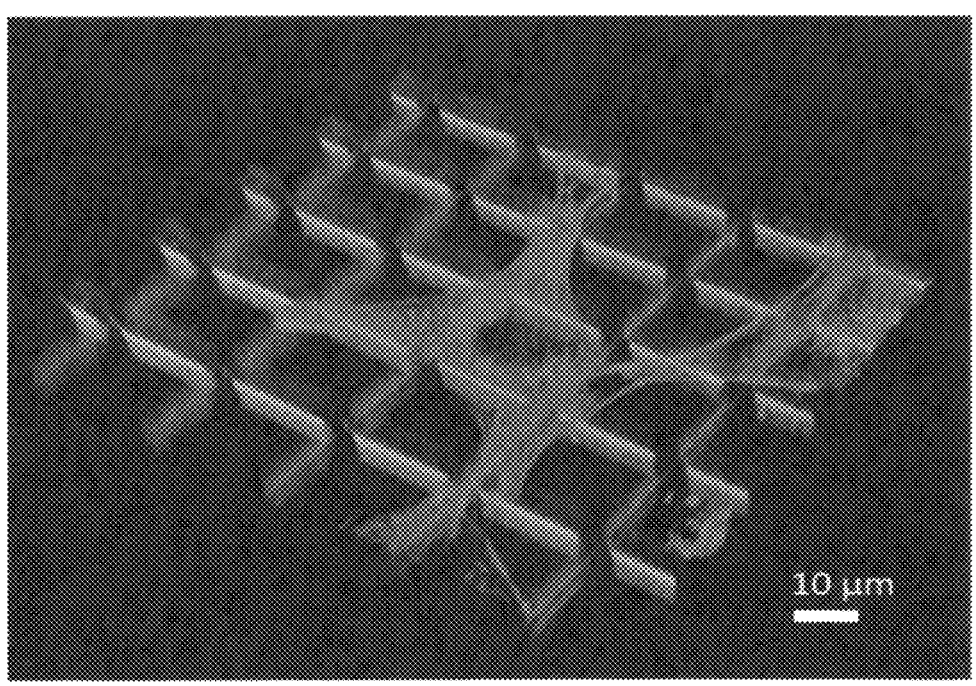
Figure 15:
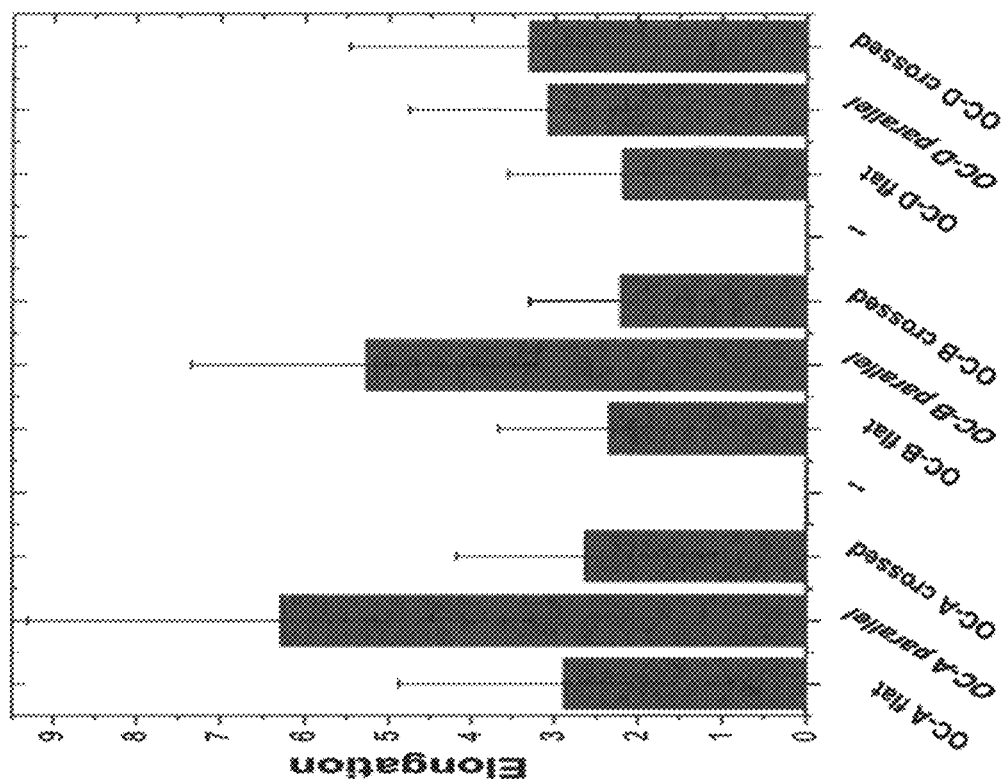
FIG. 15: Sphericity and elongation of 3T3 cells on unstructured (flat) and TPA structured substrate (parallel and crossed lines) of the composites OC-A, OC-B and OC-D based on three-dimensional fluorescence images.
Figure 15:
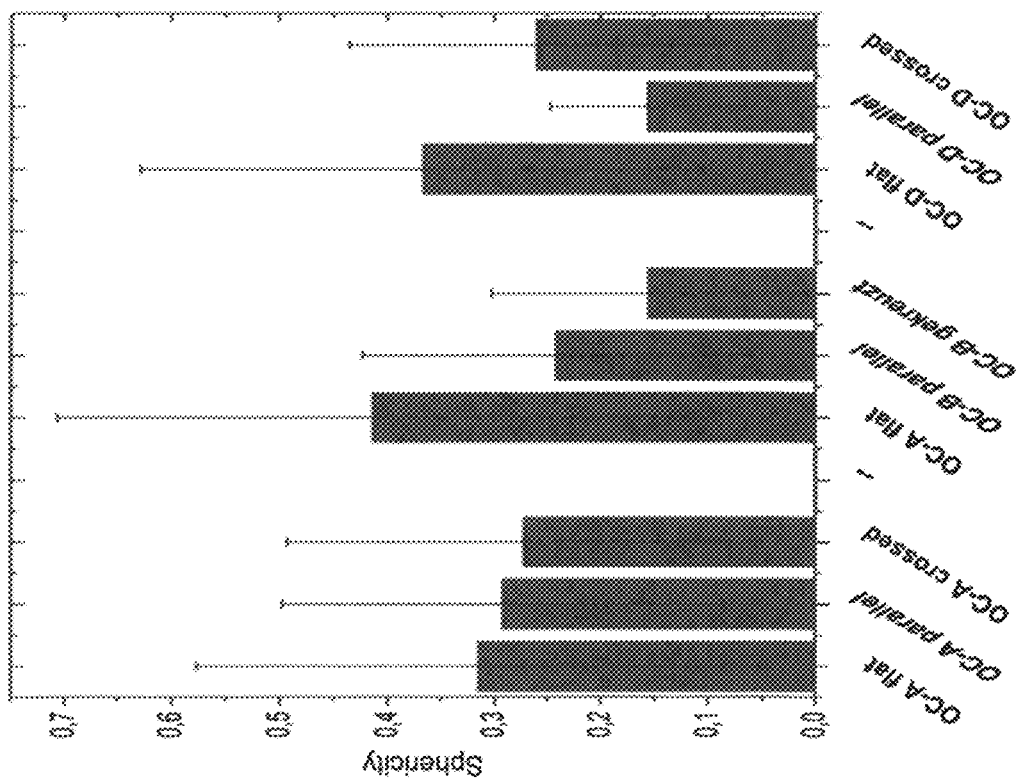

The 3T3 cells used were stably transfected mouse fibroblasts whose cytoskeleton is labelled on actin with the dye LifeAct-mCherry. They were cultivated in DMEM medium (Life Technologies Corporation, USA) enriched with 2 mM L-glutamine (Life Technologies Corporation, USA), 10% fetal calf serum (Bio&SELL GmbH, Feucht/Nuremberg) and 1% penicillin streptomycin. The samples were first placed in a 6-well microtiter plate, rinsed with a phosphate-buffered salt solution and cultured with DMEM medium for one hour. Subsequently 2 ml cell suspension with a density of $1 \times 10^5$ cells/ml were pipetted onto the structures. The cells were incubated for at least 48 hours and then examined three-dimensionally with a fluorescence microscope (TCS SP8 X, Leica, Wetzlar) (FIG. 14). The 3D images were processed with the software Fiji (based on ImageJ, National Institutes of Health, USA) with various filters and binary 3D images were generated. These were evaluated with the MorphoLibJ plugin to compare the morphology of the cells on the different substrates. For each composite, cells were compared on the unstructured areas, the parallel lines and the crossed lines. FIG. 15 shows the sphericity and elongation of the cells in 3D. The sphericity of the cells on OC-A was hardly influenced by the line structures. In contrast, for OC-B and OC-D there is a strong influence of the particles. In the flat areas the sphericity is strongly increased compared to OC-A, while in the structured areas it is reduced. The elongation is very high for OC-A and OC-B, especially for the parallel lines, since the cells are aligned with the lines. Only in OC-D this is not the case, and the influence of surface roughness appears to be higher than the microstructures of the lines. Overall, it was shown that surface roughness and microstructuring can influence cell behavior. This can be achieved here within a sample without any further process step.

Figure 16:
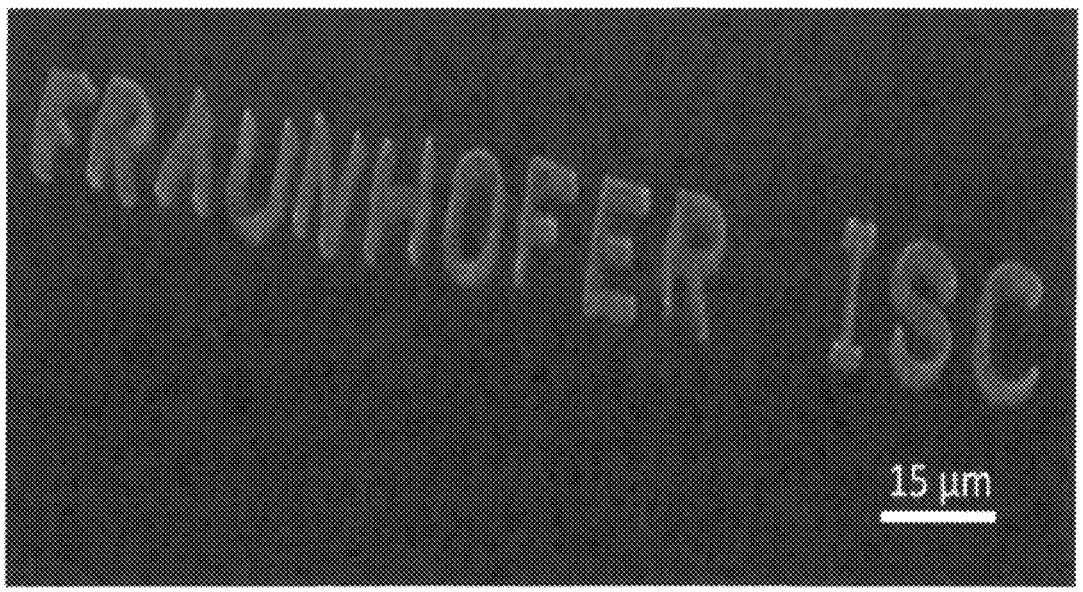
FIG. 16: TPA-structured composite consisting of a partially biodegradable ORMOCER® matrix and mesoporous silica particles filled with a fluorescent dye and coated with polyvinylpyrrolidone. (A): three-dimensional fluorescence microscope image. (B): Scanning electron microscope image of the surface.
Figure 16:
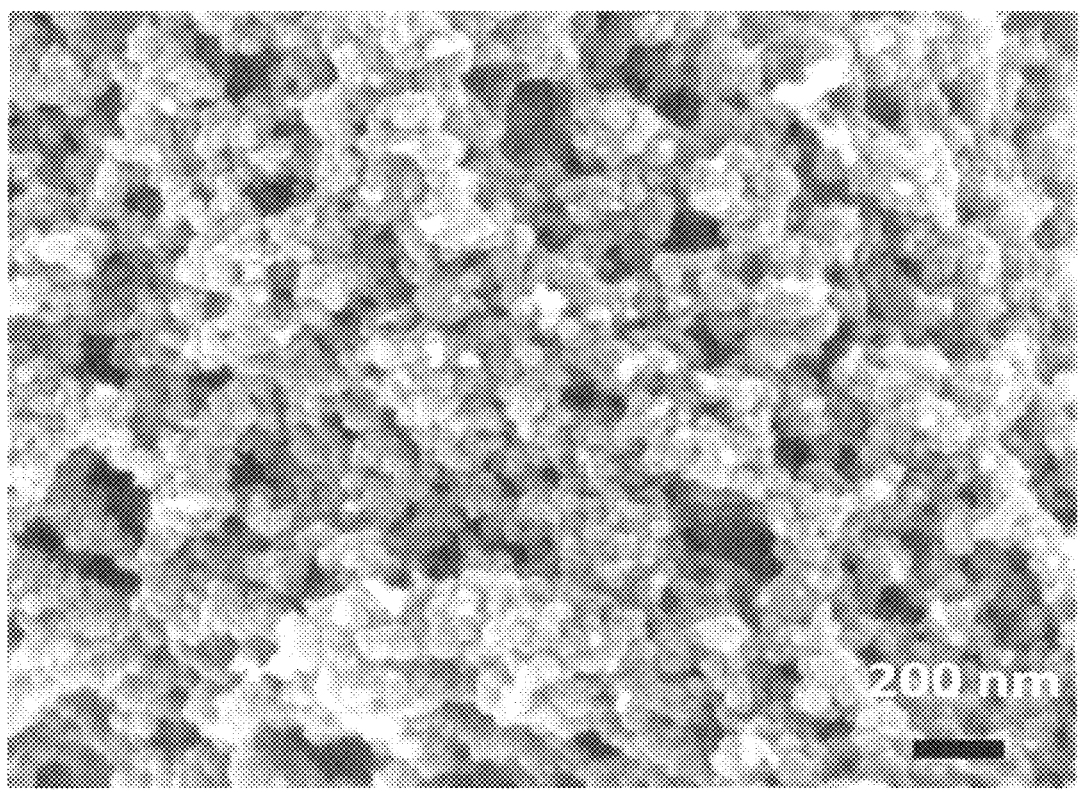

TPA Composite Structures of Biodegradable ORMOCER® with Dye-Filled Mesoporous Silica Particles Mesoporous silicon nanoparticles with a diameter of 80 nm were filled with the dye 5(6)-tetramethylrhodamine isothiocyanate and provided with a polyvinylpyrrolidone (PVP) shell. The partially biodegradable ORMOCER® described in WO2016037871 A1 was used as matrix material. The particles were stirred into the matrix at a filling level of 10% by volume and homogenized in an ultrasonic bath. The PVP shell protects the dye from leakage as long as the nanoparticles are present in the ORMOCER® matrix. However, if the shell later comes into contact with the aqueous medium, it is dissolved and the active ingredient can be released. A pulsed 80 MHz Ti:Sapphire laser (Coherent Ultra II) at a wavelength of 705 nm was used for structuring and focused into the material with an oil immersion objective (Nikon, NA=1.45) at a power of 5 mW and the sample was moved at a speed of 0.1 mm/s. The laser was then used for the structuring of the sample. FIG. 16 shows a three-dimensional fluorescence microscope image of the structure obtained and a scanning electron image of the surface showing the integration of the particles in the matrix.

LIST OF REFERENCE NUMERALS

1: Superstructures, produced by (stereo-)lithography, 3D-printing or other rapid prototyping
2: MPA fabricated submicrometer structures
3: Photostructurable ORMOCER® matrix
4: (Mesoporous) nanoparticles
5: Chemical surface functionalization
6: Active ingredient
7: Total value of the migration phase
8: Active migration phases
9: Passive migration phases

What is claimed is:

1. A composite,
obtainable by photostructuring a photostructurable matrix material in a composite batch containing said photostructurable matrix material and nanoparticles in a volume fraction of at least 1% to form a structured matrix having nanoparticles contained therein, wherein the refractive index of said composite having nanoparticles differs by less than 0.5 from the refractive index of said composite having no nanoparticles at a wavelength selected from the range of 150 nm to 2000 nm,
wherein the composite is hierarchically structured and comprises at least one structural unit (I) of a thickness (i) selected from the range of 10 μm to 100 mm and structural units (II) branching off from the structural unit (I) of a thickness (ii) respectively selected from the range of 100 nm to 1000 μm, wherein the thickness (ii) at the branch-off points is at most half the thickness (i).

2. The composite according to claim 1 which comprises at least one structural unit (I) of a thickness (i) selected from the range of 100 μm to 50 mm, structural units (II) branching off from the structural unit (I) of a thickness (ii) respectively selected from the range of 10 μm to 1000 μm, and structural units (III) branching off from the structural units (II) of a thickness (iii) respectively selected from the range of 100 nm to 100 μm, wherein the thickness (ii) of the structural units (II) at the branch-off points from the structural unit (I) is at most half the thickness (i) and the thickness (iii) of the structural units (III) at the branch-off points from the structural units (II) is at most half the thickness (ii).

3. The composite according to claim 2, wherein a plurality of structural units (I), (II) and (III) and a plurality of branches of the structural units (II) branching off from (I) and (III) branching off from (II) are present.

4. The composite according to claim 2, wherein structural units (I), (II) and (III) are each independently planar.

5. The composite according to claim 1, wherein the composite has an inner surface and an outer surface, and wherein the inner surface is at least twice as large as the outer surface.

6. The composite according to claim 1 whose surface roughness $Z_q$ determined by scanning force microscopy is 1 to 100 nm.

7. The composite according to claim 1, wherein the mean size $D_{n,50}$ of the nanoparticles is selected from the range of 10 to 1000 nm.

8. The composite according to claim 1, wherein the matrix formed by the photostructured matrix material has a structure whose size is selected from the range of 0.1 to 100 μm, wherein the matrix has voids, and wherein the structural size of the matrix and the size of the nanoparticles are selected such that a plurality of nanoparticles may each be contained in the voids of the matrix.

9. The composite according to claim 1, wherein the nanoparticles are contained in a volume fraction of 10 to 60% and the average size of the nanoparticles is selected from the range of 30 to 600 nm.

10. A process for preparing a composite according to claim 1 containing structured matrix material and nanoparticles contained therein comprising the steps of:
(a) a step in which a composite composition comprising a photostructurable material and nanoparticles is provided,
(b) a step in which at least one polymerization reaction is carried out by irradiating the photostructurable material to form a matrix to obtain the composite,
characterized in that the refractive index of the nanoparticle composite composition differs from the refractive index of the nanoparticle-free composite composition by less than 0.5 at the wavelength of irradiation performed in the at least one polymerization reaction in step (b).

11. The process according to claim 10, wherein step (b) comprises two polymerization reactions when structural units (I) and (II) are formed or three polymerization reactions when structural units (I), (II) and (III) are formed, wherein in each of the respective polymerization reactions a part of the photopolymerizable materials is reacted.

12. The method according to claim 11, wherein the two or three polymerization reactions are effected by the presence of different photostructurable materials and/or by variation of at least one process parameter selected from irradiation wavelength, irradiation power density and irradiation duration.

13. The process according to claim 10, wherein structural units (I) are formed by a polymerization reaction and structural units (II) are formed by a further polymerization reaction and, if present, structural units (III) are formed by a further polymerization reaction.

14. A composite obtainable by a process according to claim 10.

15. A method comprising a step of culturing biological cells on the composite of claim 1.

* * * * *